United States Patent
Della Santina et al.

(10) Patent No.: US 9,211,407 B2
(45) Date of Patent: Dec. 15, 2015

(54) IMPLANTABLE VESTIBULAR PROSTHESIS

(71) Applicant: The Johns Hopkins University, Baltimore, MD (US)

(72) Inventors: Charles C. Della Santina, Towson, MD (US); Gene Yevgeny Fridman, Pikesville, MD (US); Bryce Chiang, Somerset, NJ (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 14/679,741

(22) Filed: Apr. 6, 2015

(65) Prior Publication Data

US 2015/0209580 A1 Jul. 30, 2015

Related U.S. Application Data

(60) Continuation of application No. 14/444,110, filed on Jul. 28, 2014, which is a division of application No. 13/517,224, filed as application No. PCT/US2011/021005 on Jan. 12, 2011, now Pat. No. 8,868,202.

(Continued)

(51) Int. Cl.
*A61N 1/00* (2006.01)
*A61N 1/20* (2006.01)
*A61N 1/36* (2006.01)

(52) U.S. Cl.
CPC ............ *A61N 1/205* (2013.01); *A61N 1/36032* (2013.01); *A61N 1/36103* (2013.01)

(58) Field of Classification Search
USPC ......................................................... 607/62
See application file for complete search history.

(56) References Cited

U.S. PATENT DOCUMENTS 6,314,324 B1 11/2001 Lattner et al.
6,430,443 B1 8/2002 Karell (Continued)

FOREIGN PATENT DOCUMENTS

JP 2007-144057 A 6/2007
WO WO-2004-064687 A1 8/2004

OTHER PUBLICATIONS

Baird et al., The Vestibular Nerve of the Chinchilla .2. Relation between Afferent Response Properties and Peripheral innervation Patterns in the Semicircular Canals. Journal of Neurophysiology. 60: I 988.

(Continued)

*Primary Examiner* — Nicole F Lavert
(74) *Attorney, Agent, or Firm* — Venable LLP; Henry J. Daley; George L. Howarah

(57) ABSTRACT

An implantable nerve stimulation device has a sensor system, a data processor in communication with the sensor system, and a nerve stimulation system in communication with the data processor and constructed to provide electrical stimulation to at least one branch of at least one vestibulocochlear nerve. The nerve stimulation system includes an electrode array that has a first plurality of electrodes structured to be surgically implanted in electrical communication with a superior branch of the vestibular nerve, a second plurality of electrodes structured to be surgically implanted in electrical communication with a horizontal branch of the vestibular nerve, a third plurality of electrodes structured to be surgically implanted in electrical communication with a posterior branch of the vestibular nerve, and a common crus reference electrode structured to be surgically implanted into a common crus of the vestibular labyrinth.

13 Claims, 18 Drawing Sheets

Related U.S. Application Data

(60) Provisional application No. 61/294,291, filed on Jan. 12, 2010, provisional application No. 61/301,401, filed on Feb. 4, 2010, provisional application No. 61/410,107, filed on Nov. 4, 2010.

(56) References Cited

U.S. PATENT DOCUMENTS

| | | | |
|---|---|---|---|
| 6,546,291 | B2 | 4/2003 | Merfeld et al. |
| 6,694,190 | B1 | 2/2004 | Spelman et al. |
| 7,194,314 | B1 | 3/2007 | Richter et al. |
| 7,242,985 | B1 | 7/2007 | Fridman et al. |
| 2003/0097166 | A1 | 5/2003 | Krulevitch et al. |
| 2004/0106951 | A1* | 6/2004 | Edman et al. ............ 607/2 |
| 2005/0267549 | A1 | 12/2005 | Della Santina et al. |
| 2007/0208403 | A1 | 9/2007 | Della Santina et al. |
| 2009/0312817 | A1 | 12/2009 | Hogle et al. |

OTHER PUBLICATIONS

Carey et al., Principles of applied vestibular physiology. Otolaryngology—Head & Neck Surgery. 2005.

Chiang et al., Enhancements to the Johns Hopkins Multi-Channel Vestibular Prosthesis Yield Reduced Size, Extended Battery Life, Current Steering and Wireless Control. Association for Research in Otolaryngology. 2009.

Constandinou et al., A fully-integrated semicircular canal processor for an implantable vestibular prosthesis. Electronics, Circuits and Systems, 2008.ICECS 2008.15th IEEE International Conference on. 2008.

Constandinou et al., A micropower tilt processing circuit. Biomedical Circuits and Systems Conference, 2008.BioCAS 2008.1.E.E.E. 2008.

Constandinou et al., A Neural Implant ASIC for the Restoration. of Balance in Individuals with Vestibular Dysfunction. IEEE International Symposium on Circuits and Systems (ISCAS). 2009.

Constandinou et al., A Partial-Current-Steering Biphasic Stimulation Driver for Vestibular Prostheses. Biomedical Circuits and Systems, IEEE Transactions on. 2: 2008.

Constandinou et al., An ultra-low-power micro-optoelectromechanical tilt sensor. Circuits and Systems, 2008.ISCAS 2008.IEEE International Symposium on. 2008.

Constandinou et al., Towards an Implantable Vestibular Prosthesis: The Surgical Challenges. Neural Engineering, 2007.CNE '07.3rd International IEEEIEMBS Conference on. 2007.

Davidovics et al., Linearity of Stimulus-Response .Mapping During Semicircular Canal Stimulation using a Vestibular Prosthesis. ARO 2009. 2009.

Della Santina et al., 3D Vestibuloocular reflex, afferent responses and crista histology in chinchillas after unilateral intratympanic gentamicin. Association for Research in Otolaryngology Annual Mtg. 2005.

Della Santina et al., A multichannel semicircular canal neural prosthesis using electrical stimulation to restore 3-D vestibular sensation. Ieee Transactions on Biomedical Engineering. 54: 2007.

Della Santina et al., Current and future management of bilateral loss of vestibular sensation—an update on the Johns Hopkins multichannel vestibular prosthesis project. Cochlear Implants International. 2010.

Della Santina et al., Electrical stimulation to restore vestibular function—development of a 3-D vestibular prosthesis. 27th Annual IEEE Engineering in Medicine and Biology. 2005.

Della Santina et al., Orientation of human semicircular canals-measured by three-dimensional multipianar C1 reconstruction. Jail:—Journal of the A ssociation for Research in Otolarynaology: 6: 2005.

Della Santina et al., Vestibulo—ocular reflex of chinchilla during high frequency head. rotation and electrical stimuli. Society—for Neuroscience Abstract Viewer and Itinerary Planner. 2003: 2003.

European Search Report issued in Application No. 11733323.7 dated Jul. 15, 2013.

Fridman et al., Multichannel Vestibular Prosthesis Stabilizes Eyes for Head Rotation About Any Axis. Journal of the Association for Research in Otolaryngology. Submitted 2009: 2009.

Gong et al., Prototype neural semicircular canal prosthesis using patterned electrical stimulation. Annals of Biomedical Engineering, 28: 2000.

Gong et al., System design and performance of a unilateral horizontal semicircular canal prosthesis. IEEE Transactions on Biomedical Engineering. 49: 2002.

Gong et al., Vestibulo-Ocular Responses Evoked Via Bilateral Electrical Stimulation of the Lateral Semicircular Canals. IEEE Transactions on Biomedical Engineering. 55: 2008.

Lewis et al., Cross-axis vestibular adaptation produced by patterned electrical stimulation. Neurology. 56: 2001.

Lewis et al., Vestibular adaptation studied with a prosthetic semicircular canal. Journal of Vestibular Research—Equilibrium & Orientation. 12: 2002.

Merfeld et al., Acclimation to chronic constant-rate peripheral stimulation provided by a vestibular prosthesis. IEEE Transactions on Biomedical Engineering. 53: 2006.

Merfeld et al., Chronic vestibulo-ocular reflexes evoked by a vestibular prosthesis. IEEE Transactions on Biomedical Engineering. 54: 2007.

Patent Examination Report issued in Australian Application No. 2011205324 dated Jul. 29, 2013.

Phillips et al., A multichannel vestibular prosthesis based on cochlear implant technology. Society for Neuroscience. 2008.

Shkel et al., An electronic prosthesis mimicking the dynamic vestibular function. Audiology and Neuro-Otology. 1.1: 2006.

Spelman, Electrodes and Stimulators for Strial Presbycusis. Thirty Fourth Neural Prosthesis Workshop . 2010. Oct. 12, 2003.

Tang et al., Effects of semicircular canal electrode implantation on hearing in chinchillas. Acta Oto-Laryngologica. 129: 2009.

Wall et al., Vestibular prostheses; The engineering and biomedical issues. Journal of Vestibular Research-Equilibrium & Orientation. 12: 2002.

* cited by examiner

IMPLANTABLE VESTIBULAR PROSTHESIS

CROSS-REFERENCE OF RELATED APPLICATION

This application is a Continuation of U.S. patent application Ser. No. 14/444,110 filed Jul. 28, 2014, which is a Divisional of U.S. patent application Ser. No. 13/517,224 filed Jun. 19, 2012, which is a National Stage of International Patent Application No. PCT/US2011/021005 filed Jan. 12, 2011, and claims priority to U.S. Provisional Application Nos. 61/294,291 filed Jan. 12, 2010; 61/301,401 filed Feb. 4, 2010; and 61/410,107 filed Nov. 4, 2010. The entire contents of each of these applications are hereby incorporated by reference.

This invention was made with Government support of Grant Nos. R01DC9255, K08DC6216, and 5F32DC009917, awarded by the Department of Health and Human Services, the National Institutes of Health. The U.S. Government has certain rights in this invention.

BACKGROUND

1. Field of Invention

The field of the currently claimed embodiments of this invention relates to systems and components for stimulating nerves, and more particularly to systems that include surgically implantable vestibular prostheses and components, algorithms, stimulus protocols and methods for surgically implantable vestibular prostheses.

2. Discussion of Related Art

In normal individuals, the two inner ear labyrinths modulate activity on afferent fibers within each vestibular nerve branch so as to provide the central nervous system (CNS) with sensation of rotational head motion and linear accelerations due to both gravity and translational motion (termed gravitoinertial acceleration). Each labyrinth contains three mutually orthogonal semicircular canals (SCCs) to sense head rotation. Each SCC modulates activity on its branch of the vestibular nerve approximately in time with the component of 3-dimensional (3D) head angular velocity about the axis of that SCC. (See FIG. 1.) Each SCC is approximately coplanar with an SCC in the opposite ear, and each coplanar pair of SCC effectively acts as a pair of antiparallel angular rate sensors. The SCCs, oriented in the horizontal, left-anterior-right-posterior (LARP), and right-anterior-left-posterior (RALP) axes, are responsible for sensing angular velocity in those respective axes, and the two otolith end organs (the utricle and saccule) are responsible for sensing gravitoinertial (translational) accelerations. These sensory inputs drive compensatory reflexes that stabilize gaze and posture so as to maximize clarity of vision during head movement and to prevent falls. Patients who have lost vestibular hair cell function in both labyrinths can suffer from debilitating loss of visual acuity and balance because their CNS no longer receives normal head movement information or gravitational orientation cues. While compensatory use of visual and proprioceptive input might partially supplant lost labyrinthine input, this strategy fails during high frequency, high acceleration, transient head motions, such as those experienced while walking (Carey, J. P. and C. C. Della Santina. Principles of applied vestibular physiology. Otolaryngology—Head & Neck Surgery. 2005). Approximately 0.1% of U.S. adults report a constellation of symptoms consistent with severe bilateral vestibular hypofunction, corresponding to more than 250,000 individuals in the U.S. alone (Della Santina, C. C., A. A. Migliaccio, R. Hayden, T. A. Melvin, G. Y. Fridman, B. Chiang, N. S. Davidovics, C. Dai, J. P. Carey, L. B. Minor, I. C. W. Anderson, H. Park, S. Lyford-Pike, and S. Tang. Current and future management of bilateral loss of vestibular sensation—an update on the Johns Hopkins multichannel vestibular prosthesis project. Cochlear Implants International. 2010). For those who fail to compensate through rehabilitation exercises, no adequately effective treatment exists. A multichannel vestibular prosthesis that directly modulates activity of surviving vestibular afferents based on motion sensor input could improve quality of life for vestibular-deficient individuals if it effectively restores sensation of head motion and gravitational orientation (Della Santina et al., supra; Wall, C., D. M. Merfeld, S. D. Rauch, and F. O. Black. Vestibular prostheses: The engineering and biomedical issues. Journal of Vestibular Research-Equilibrium & Orientation. 12: 2002).

Gong and Merfeld described the first head-mounted vestibular prosthesis in 2000 (Gong, W. S. and D. M. Merfeld. Prototype neural semicircular canal prosthesis using patterned electrical stimulation. Annals of Biomedical Engineering. 28: 2000; Gong, W. S, and D. M. Merfeld. System design and performance of a unilateral horizontal semicircular canal prosthesis. IEEE Transactions on Biomedical Engineering. 49: 2002; Merfeld et al U.S. Pat. No. 6,546,291 B2). That device is capable of sensing head rotation about one axis and electrically stimulating the vestibular nerve via a pair of electrodes intended to excite afferents in an ampullary nerve innervating one SCC. Using this device, Gong, Merfeld et al. were able to partially restore the Vestibulo-Ocular Response (VOR) about one axis in squirrel monkeys and guinea pigs. They have since described long-term changes in the prosthetically-evoked VOR, postural effects, and responses to simultaneous, bilateral stimulation of the lateral SCCs (Gong, W. S., C. Haburcakova, and D. M. Merfeld. Vestibulo-Ocular Responses Evoked Via Bilateral Electrical Stimulation of the Lateral Semicircular Canals, IEEE Transactions on Biomedical Engineering. 55: 2008; Gong, W. S. and D. M. Merfeld. Prototype neural semicircular canal prosthesis using patterned electrical stimulation. Annals of Biomedical Engineering. 28: 2000; Gong, W. S. and D. M. Merfeld. System design and performance of a unilateral horizontal semicircular canal prosthesis. IEEE Transactions on Biomedical Engineering. 49: 2002; Lewis, R. F., W. S. Gong, M. Ramsey, L. Minor, R. Boyle, and D. M. Merfeld. Vestibular adaptation studied with a prosthetic semicircular canal. Journal of Vestibular Research-Equilibrium & Orientation. 12: 2002; Lewis, R. F., D. M. Merfeld, and W. S. Gong. Cross-axis vestibular adaptation produced by patterned electrical stimulation. Neurology. 56: 2001; Merfeld, D. M., W. S. Gong, J. Morrissey, M. Saginaw, C. Haburcakova, and R. F. Lewis, Acclimation to chronic constant-rate peripheral stimulation provided by a vestibular prosthesis. IEEE Transactions on Biomedical Engineering. 53: 2006; Merfeld, D. M., C. Haburcakova, W. Gong, and R. F. Lewis. Chronic vestibulo-ocular reflexes evoked by a vestibular prosthesis. IEEE Transactions on Biomedical Engineering. 54: 2007).

Della Santina et al. (Della Santina, C. C., A. A. Migliaccio, and A. H. Patel. Electrical stimulation to restore vestibular function—development of a 3-D vestibular prosthesis. 27th Annual IEEE Engineering in Medicine and Biology. 2005; Della Santina, C. C., A. A. Migliaccio, and A. H. Patel. A multichannel semicircular canal neural prosthesis using electrical stimulation to restore 3-D vestibular sensation. IEEE Transactions on Biomedical Engineering. 54: 2007) described a multichannel vestibular prosthesis (here denoted MVP1, for Multichannel Vestibular Prosthesis, version 1) capable of sensing angular velocity about three orthogonal axes and asynchronously stimulating each of the three ampullary nerves of a single labyrinth, allowing partial restoration of VOR responses for head rotation about any axis. Increasing the number of stimulating electrodes and the current amplitude resulted in spatial current spread within the implanted labyrinths which limited the ability to selectively stimulate the appropriate bundle of vestibular afferents. Increasing current amplitude initially increased the VOR magnitude without changing the intended rotational axis, but at higher amplitudes, the eye rotation axis deviated from ideal for the target SCC, as current spread to other bundles of vestibular afferents. Subsequent studies by Della Santina et al. have used the MVP1 to study optimization of stimulus coding strategy, a coordinate system orthogonalization approach to minimizing 3D misalignment errors, effects of vestibular electrode implantation on hearing, and changes in 3D VOR alignment during chronic prosthetic stimulation (Della Santina, C. C., A. A. Migliaccio, R. Hayden, T. A. Melvin, G. Y. Fridman, B. Chiang, N. S. Davidovics, C. Dai, J. P. Carey, L. B. Minor, I. C. W. Anderson, H. Park, S. Lyford-Pike, and S. Tang. Current and future management of bilateral loss of vestibular sensation—an update on the Johns Hopkins multichannel vestibular prosthesis project. Cochlear Implants International. 2010; Chiang, B., G. Y. Fridman, and C. C. Della Santina. Enhancements to the Johns Hopkins Multi-Channel Vestibular Prosthesis Yield Reduced Size, Extended Battery Life, Current Steering and Wireless Control. Association for Research in Otolaryngology. 2009; Davidovics, N., G. Y. Fridman, and C. C. Della Santina. Linearity of Stimulus-Response Mapping During Semicircular Canal Stimulation using a Vestibular Prosthesis. ARO 2009. 2009; Della Santina, C. C., A. A. Migliaccio, and L. B. Minor. Vestibulo—ocular reflex of chinchilla during high frequency head rotation and electrical stimuli. Society for Neuroscience Abstract Viewer and Itinerary Planner. 2003: 2003; Della Santina, C. C., A. A. Migliaccio, H. J. Park, I. C. W. Anderson, P. Jiradejvong, L. B. Minor, and J. P. Carey. 3D Vestibuloocular reflex, afferent responses and *crista* histology in chinchillas after unilateral intratympanic gentamicin. Association for Research in Otolaryngology Annual Mtg. 2005; Della Santina, C. C., A. A. Migliaccio, and A. H. Patel. Electrical stimulation to restore vestibular function—development of a 3-D vestibular prosthesis. 27th Annual IEEE Engineering in Medicine and Biology. 2005; Della Santina, C. C., A. A. Migliaccio, and A. H. Patel. A multichannel semicircular canal neural prosthesis using electrical stimulation to restore 3-D vestibular sensation, Ieee Transactions on Biomedical Engineering. 54: 2007; Della Santina, C. C., V. Potyagaylo, A. A. Migliaccio, L. B. Minor, and J. P. Carey. Orientation of human semicircular canals measured by three-dimensional multiplanar CT reconstruction. Jaro-Journal of the Association for Research in Otolaryngology. 6: 2005; Fridman, G. Y., N. Davidovics, C. Dai, and C. C. Della Santina. Multichannel Vestibular Prosthesis Stabilizes Eyes For Head Rotation About Any Axis. Journal of the Association for Research in Otolaryngology. Submitted 2009: 2009; Tang, S., T. A. N. Melvin, and C. C. Della Santina. Effects of semicircular canal electrode implantation on hearing in chinchillas. Acta Oto-Laryngologica. 129: 2009). Della Santina and Faltys described a hybrid cochlear and vestibular stimulator.

Shkel et al, Constandinou et al, and Phillips et al have also described vestibular prosthesis circuits but have not published results obtained from physiological testing (Shkel, A. M. and F. G. Zeng. An electronic prosthesis mimicking the dynamic vestibular function. Audiology and Neuro-Otology. 11: 2006; Constandinou, T. and J. Georgiou. A micropower tilt processing circuit. Biomedical Circuits and Systems Conference, 2008.BioCAS 2008.IEEE. 2008; Constandinou, T., J. Georgiou, and C. Andreou. An ultra-low-power micro-optoelectromechanical tilt sensor, Circuits and Systems, 2008.ISCAS 2008.IEEE International Symposium on. 2008; Constandinou, T., J. Georgiou, C. Doumanidis, and C. Toumazou. Towards an Implantable Vestibular Prosthesis: The Surgical Challenges, Neural Engineering, 2007.CNE '07.3rd International IEEE/EMBS Conference on. 2007; Constandinou, T., J. Georgiou, and C. Toumazou. A fully-integrated semicircular canal processor for an implantable vestibular prosthesis. Electronics, Circuits and Systems, 2008.ICECS 2008.15th IEEE International Conference on. 2008; Constandinou, T., J. Georgiou, and C. Toumazou. A Neural Implant ASIC for the Restoration of Balance in Individuals with Vestibular Dysfunction. IEEE International Symposium on Circuits and Systems (ISCAS). 2009; Constandinou, T., J. Georgiou, and C. Toumazou. A Partial-Current-Steering Biphasic Stimulation Driver for Vestibular Prostheses. Biomedical Circuits and Systems, IEEE Transactions on. 2: 2008; Phillips, J., S. Bierer, A. Fucks, C. Kaneko, L. Ling, K. Nie, T. Oxford, and J. Rubinstein. A multichannel vestibular prosthesis based on cochlear implant technology. Society for Neuroscience. 2008). Shkel et al described a custom-designed micro-electro-mechanical system (MEMs) gyroscope and a hardware-based solution for setting the pattern of electrical stimulation. Instead of using a microcontroller to determine pulse timing, Shkel et al developed a control circuit, which emulated the transfer function of SCC canal dynamics determined experimentally by Fernandez, Goldberg, et al (Baird, R. A., G. Desmadryl, C. Fernandez, and J. M. Goldberg. The Vestibular Nerve of the Chinchilla 0.2. Relation between Afferent Response Properties and Peripheral Innervation Patterns in the Semicircular Canals. Journal of Neurophysiology. 60: 1988). Constandinou et al described a vestibular prosthesis Application Specific Integrated Circuit (ASIC) and corresponding ASIC components, which could result in a smaller implant. As was the case with Shkel et al's device, the control circuit used in Constandinou et al's device is a circuit realization of the canal dynamics transfer function. To date, no physiological animal experiments have been reported by either Shkel et al or Constandinou et al. Phillips et al described a commercially available cochlear implant modified for use as a vestibular prosthesis.

All prosthetic vestibular nerve stimulation studies to date have encountered performance constraints due to suboptimal electrode-nerve coupling and selectivity, as well as limitations related to device size and power consumption. No vestibular prosthesis yet described and produced has included sensors of both rotation and gravitoinertial/translational acceleration or multiple current sources able to support multipolar "current steering" stimulus paradigms, nor has any yet achieved sufficient combination of miniaturization, system integration, multidimensional sensing, in situ self-testing ability and reduction in power consumption to constitute a prosthesis appropriate for long-term restoration of the VOR in vestibular-deficient patients.

The six semicircular canals located in the two inner ears (three in each ear) provide balance information to the brain by sensing the rotation of the head about three orthogonal axes, corresponding to the spatial orientation of each of the canals. A vestibular prosthesis can emulate this function by sensing the 3D rotation and linear acceleration of the head with three orthogonally oriented gyroscopes and linear accelerometers. The sensation of head rotation is transmitted to the brain by electrically stimulating the three corresponding branches of the vestibular nerve that normally carry such information from each of the semicircular canals in the implanted ear. The sensation of head linear acceleration is transmitted to the brain by electrically stimulating the three corresponding branches of the vestibular nerve that normally carry such information from the utricle and saccule in the implanted ear.

Recent advances in the development of vestibular prostheses demonstrated that current spread can severely degrade the precision with which the prosthesis can selectively target each of the branches of the vestibular nerve. Functionally, current spread causes misalignment between the sensed axis of head rotation and the axis of rotation that is conveyed via the electrical stimulation delivered to the vestibular nerve. This is because the stimulation current which is intended to deliver stimulation to only one of the branches of the nerve can spread to the neighboring branches, unintentionally stimulating them as well. The amount of current spread depends upon proximity of the electrode to the targeted nerve branch and path of the electrical current flowing through the tissue during stimulation. Thus accurate surgical placement of the electrode contact in close proximity to each of the intended stimulation sites and away from the untargeted branches of the nerve is critical to the operation of the prosthesis. Because the branches of the vestibular nerve are very near each other, such surgical placement can be difficult without causing damage to the delicate neural structures (ampullae), where the vestibular nerve enters the semicircular canals (SCCs). These entry points are targeted for electrical stimulation in each canal (FIG. 1).

There thus remains a need for improved implantable vestibular prostheses that facilitate accurate placement of electrodes and precise delivery of stimulus current while minimizing difficulty and variability of surgical implantation.

SUMMARY

An implantable nerve stimulation device according to an embodiment of the current invention has a sensor system, a data processor in communication with the sensor system, and a nerve stimulation system in communication with the data processor and constructed to provide electrical stimulation to at least one branch of at least one vestibulocochlear nerve. The nerve stimulation system includes an electrode array that has a first plurality of electrodes structured to be surgically implanted in electrical communication with a superior branch of the vestibular nerve, a second plurality of electrodes structured to be surgically implanted in electrical communication with a horizontal branch of the vestibular nerve, a third plurality of electrodes structured to be surgically implanted in electrical communication with a posterior branch of the vestibular nerve, and a common crus reference electrode structured to be surgically implanted into a common crus of the vestibular labyrinth.

An electrical lead for an implantable nerve stimulation device according to an embodiment of the current invention has a first plurality of wires and a first plurality of electrodes in electrical contact with a corresponding one of the first plurality of wires, the first plurality of electrodes forming a superior vestibular nerve branch electrode array such that the first plurality of electrodes are held substantially fixed with respect to each other; a second plurality of wires and a second plurality of electrodes in electrical contact with a corresponding one of the second plurality of wires, the second plurality of electrodes forming a horizontal vestibular nerve branch electrode array such that the second plurality of electrodes are held substantially fixed with respect to each other; a third plurality of wires and a third plurality of electrodes in electrical contact with a corresponding one of the third plurality of wires, the third plurality of electrodes forming a posterior vestibular nerve branch electrode array such that the third plurality of electrodes are held substantially fixed with respect to each other; and a reference electrode in electrical connection with a corresponding reference wire.

An implantable vestibular stimulation device according to an embodiment of the current invention has a sensor system that includes a rotational sensor system and an orientation sensor system, both of which are fixed with respect to the implantable vestibular stimulation device, a data processor in communication with the sensor system, a data storage system in communication with the data processor, and a vestibular nerve stimulation system in communication with the data processor. The orientation sensor system senses an orientation of the implantable vestibular stimulation device relative to a local gravitational field to provide an orientation signal. The data processor is configured to generate an alignment transformation matrix based on the orientation signal and information regarding an orientation of a head-fixed reference frame of a head in which the implantable vestibular stimulation device is implanted such that the alignment transformation matrix can be stored in the data storage system, and the data processor is configured to receive rotation signals from the rotational sensor system and correct the rotation signals using the alignment transformation matrix to provide corrected rotational signals to the vestibular nerve stimulation system.

An electrode for the electrical stimulation of a nerve according to an embodiment of the current invention has an electrically insulating structure defining a chamber and providing an opening for electrical contact with a nerve, an electrically conducting structure disposed at least partially within the chamber, and an electrolyte disposed in the chamber in electrical contact with the electrically conducting structure.

BRIEF DESCRIPTION OF THE DRAWINGS

Further objectives and advantages will become apparent from a consideration of the description, drawings, and examples.

FIG. 11B: Pulse Rate Modulation based on Linear Accelerometer Input). Pulse rate modulation of the corresponding stimulation channel (on the HS, P, U or S electrode arrays) by signals reported by each of six motion sensors is shown during sinusoidal motor rotation at 1 Hz with a peak velocity of 50°/s. Pulse recordings were taken on three channels concurrently; the implant was then realigned to bring another accelerometer in line with the motor's rotational axis. These traces show the modulation on three channels by linear accelerometers when the prosthesis is offset from the motor's center of rotation by 20 cm.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

Figure 2:
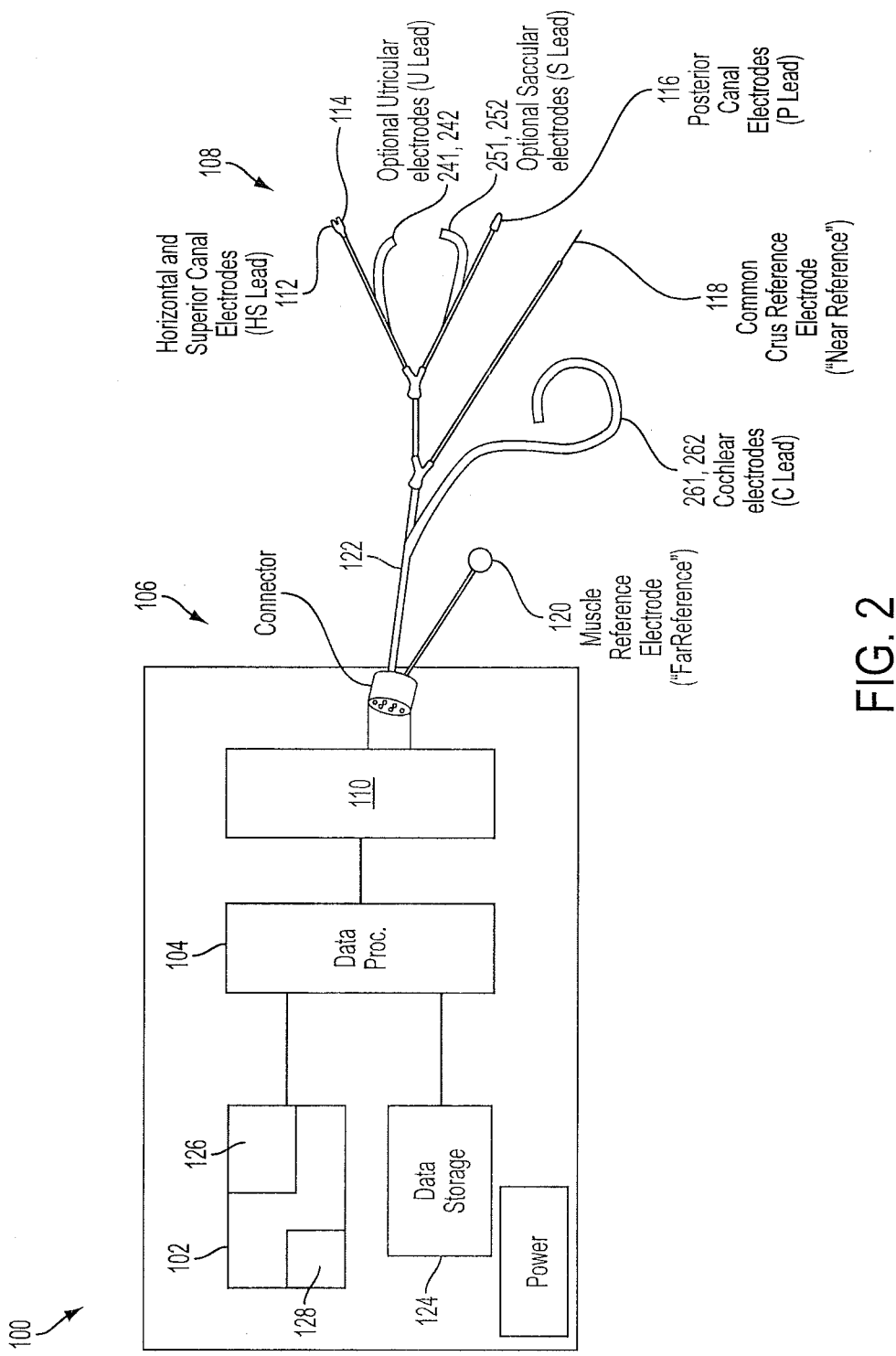
FIG. 2 is a schematic illustration of an implantable vestibular stimulation device according to an embodiment of the current invention. In this example, electronics for sensing head motion, storing data, computing stimulus timing, generating stimulus currents, measuring electrode potentials and sensing neural responses are housed along with a battery and antenna for power and signal transmission in a package (either implanted in a hermetically sealed container or connected to the electrode arrays via a percutaneous link).

FIG. 2 provides a schematic illustration of an implantable vestibular stimulation device 100 according to an embodiment of the current invention. The implantable vestibular stimulation device 100 includes a sensor system 102, a data processor 104 in communication with the sensor system 102, and a vestibular nerve stimulation system 106 in communication with the data processor 104. The vestibular nerve stimulation system 106 is constructed to provide electrical stimulation to a vestibular nerve of a user of the device. The vestibular nerve stimulation system 106 includes an electrode array 108. In some embodiments, the vestibular nerve stimulation system 106 includes additional electronic components 110.

The electronics 110 contain plurality of digital-to-analog converters to command a plurality of current sources and current sinks, or voltage controlled current sources (VCCS). The component also contains a plurality of switches to connect any electrode to any VCCS. This capability allows the current to flow from any combination of electrodes to any other combination of electrodes to allow current steering. Current steering can be used to more selectively target each branch of the vestibular nerve. By commanding the digital-to-analog converters and switches, data processor 104 controls both the timing and amplitude of the stimulation pulses. Additional electronics in 110 contain one or more amplifiers to measure impedance or neural response potentials across any two electrodes.

The electrode array 108 of said vestibular nerve stimulation system 106 includes a first plurality of electrodes 112 structured to be surgically implanted in electrical contact with a superior branch of the vestibular nerve, a second plurality of electrodes 114 structured to be surgically implanted in electrical contact with a horizontal branch of the vestibular nerve, a third plurality of electrodes 116 structured to be surgically implanted in electrical contact with a posterior branch of the vestibular nerve, and a common crus reference electrode 118 structured to be surgically implanted into a common crus labyrinth of a vestibular system. The electrode array 108 of the vestibular nerve stimulation system 106 can also include a second reference electrode 120 structured to be fixed in electrical contact in a region proximate and external to the vestibular system. For example, the second reference electrode 120 could be surgically implanted in muscle tissue or attached externally and relatively close to the vestibular system. The first and second reference electrodes can also be viewed as "near" and "far" reference electrodes, respectively. The electrode array 108 of the vestibular nerve stimulation system 106 can also include a lead with a plurality of electrodes 241 for implantation and stimulation of the utricle (U lead, 242). The electrode array 108 of the vestibular nerve stimulation system 106 can also include a lead with a plurality of electrodes 251 for implantation and stimulation of the saccule (S lead, 252). The electrode array 108 of the vestibular nerve stimulation system 106 can also include a lead with a plurality of electrodes 261 for implantation and stimulation of the cochlea (C lead, 262).

The implantable vestibular stimulation device 100 can be a stand-alone device in some embodiments or could be incorporated as a component of another device. For example, some embodiments can incorporate implantable vestibular device 100 with a cochlear implant, and some embodiments can incorporate a wireless interface for transmission of signals and power.

Each of the first 112, second 114 and third 116 pluralities of electrodes can be three-electrode arrays structured to facilitate implantation in electrical contact respectively with the superior, horizontal and posterior branches of the vestibular nerve. The electrodes 112, 114, 116, 118 and 122 can be structured together in a single lead structure 122, as illustrated in FIG. 2, to facilitate surgical implantation. For example, the lead 22 can be a novel "self aligning" lead structure according to an embodiment, as will be described in more detail below. However, other lead structures can also be used in this embodiment of the current invention.

In some embodiments of the current invention, the electronic components 110 of the vestibular nerve stimulation system 106 can include a plurality of current sources and a plurality of current sinks, each of which can be selectively directed to at least one electrode of the first plurality of electrodes 112, the second plurality of electrodes 114, the third plurality of electrodes 116, the far reference electrode, and the common crus reference electrode 118. This can be used, for example, to provide current steering to control stimulation of the particular nerve branches. This can be useful, for example, when nerves or nerve branches, such as the superior and horizontal branches of the vestibular nerve, are close together. An example of such an embodiment for the electronic components 110 will be described in more detail below. In an embodiment of the current invention, the data processor 104 can be adapted to receive information concerning a degree of stimulation of at least one of the superior, horizontal, posterior, utricular and saccular branches of the vestibular nerve and to provide a corrected signal to the vestibular nerve stimulation system to effect current steering to improve electrical stimulation of the vestibular nerve. In an embodiment of the current invention, the data processor 104 can be adapted to receive information concerning a degree of stimulation of at least one branch of the vestibulocochlear nerve and to provide a corrected signal to the nerve stimulation system to effect current steering to improve electrical stimulation of the vestibulocochlear nerve.

In some embodiments of the current invention, the implantable vestibular stimulation device 100 can further include a data storage system 124 that is in communication with the data processor 104. The data storage system 124 can be volatile or non-volatile memory, for example. In some embodiments, the data storage system 124 can be configured to store data for use by the data processor 104 to correct signals received from said sensor system 102, for example.

The data processor 104 can be configured to correct for misalignment between the implantable vestibular stimulation device 100 and a head-fixed reference frame, misalignment of the electrode array 118 with the vestibular nerve and/or current spread during stimulation of the vestibular nerve according to some embodiments of the current invention. Such embodiments will be described in more detail below.

The sensor system 102 can include a three-axis gyroscope system 126 according to some embodiments of the current invention. For example, micro-electromechanical systems (MEMS) gyroscope systems are suitable for some embodiments of the current invention. The sensor system 102 can further include an orientation sensor system 128 according to some embodiments of the current invention, A three-axis system of linear accelerometers can be used for the orientation sensor system in some embodiments. For example, MEMS linear accelerometers are suitable for some embodiments. The use of a three-axis linear accelerometer system for the orientation sensor can provide an addition benefit of also providing gravito-inertial signals for stimulation the corresponding nerves in some embodiments. The system can also include an acoustic sensor, for detection of signals necessary to compute appropriate stimulation currents on the U, S and C leads to the utricle, saccule and cochlea, respectively.

Figure 3:
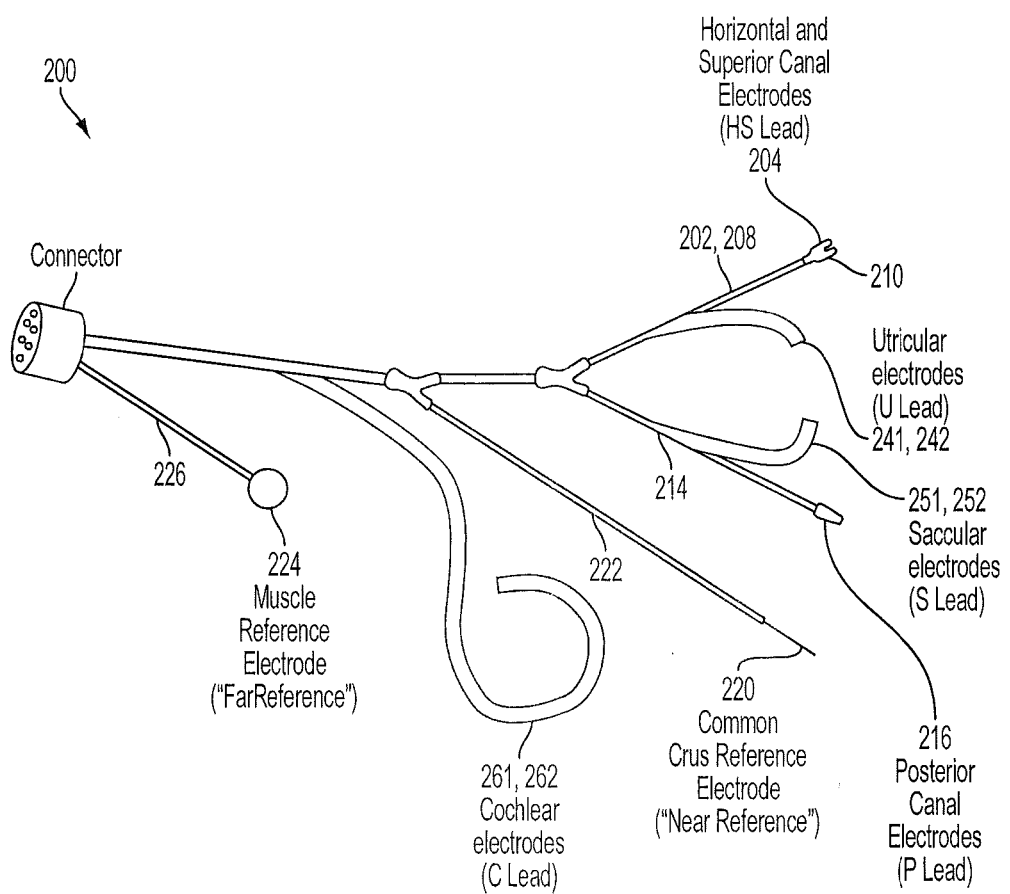
FIG. 3 is an illustration of an electrical lead according to an embodiment of the current invention. In this example, the connector contains a plurality of contacts, which connect with a separate Par wires to each of the electrode contacts on the P (3 contacts) and HS (6 contacts) leads, and the two reference electrodes. Electrode arrays for stimulation of the utricle (U lead, which contains one or more electrodes), the saccule (S lead, which contains one or more electrodes), and the cochlea (C lead, which contains one or more electrodes) are optionally included. In this example, the entire array is composed of flexible medical grade silicone with the PtIr wires running inside the silicone from the connector to each of the electrode contacts. Other insulators and types of wire may be used. The wires are coiled, corrugated, or otherwise bent at intervals inside the silicone along the length of the electrode to provide stress relief during stretching and bending of the leads. A "Far" reference electrode is designed to be implanted outside the inner ear, typically beneath head or neck musculature. A "Near" reference electrode is designed to be implanted within the common crus of the inner ear (the junction of the superior and posterior SCCs), to allow control of the direction of stimulus currents emitted by other electrodes. Electrode wires can connect to either a percutaneous connector or directly to a hermetically sealed, implantable package containing stimulation electronics. The connector is designed to allow in situ replacement of the electronics package without removal of the electrode arrays from the inner ear.

FIG. 3 is an illustration of an electrical lead 200 for an implantable vestibular stimulation device according to an embodiment of the current invention. The electrical lead 200 can be used for lead 122 in the implantable vestibular stimulation device 100, for example. However, the implantable vestibular stimulation device 100 is not limited to only this embodiment for lead 122. The electrical lead 200 includes a first plurality of wires 202 and a first plurality of electrodes 204 that are in electrical contact with a corresponding subset of the first plurality of wires 202. The first plurality of wires 202 are enclosed within an electrically insulating structure and cannot be individually seen in FIG. 3. See FIG. 4 for a more detailed illustration of the first plurality of electrodes 204. The first plurality of electrodes 204 form a superior vestibular nerve branch electrode array 206 such that the first plurality of electrodes 204 are held substantially fixed with respect to each other. The electrical lead 200 also includes a second plurality of wires 208 (also not individually illustrated in FIG. 3) and a second plurality of electrodes 210 that are in electrical contact with a corresponding subset of the second plurality of wires 208. The second plurality of electrodes 210 form a horizontal vestibular nerve branch electrode array 212 such that the second plurality of electrodes 210 are held substantially fixed with respect to each other. The electrical lead 200 also includes a third plurality of wires 214 and a third plurality of electrodes 216 that are in electrical contact with a corresponding subset of the third plurality of wires 214. The third plurality of electrodes 216 form a posterior vestibular nerve branch electrode array 218 such that the third plurality of electrodes 216 are held substantially fixed with respect to each other. The electrical lead 200 also includes a fourth plurality of wires 241 and a fourth plurality of electrodes 242 (also not individually illustrated in FIG. 3) that are in electrical contact with a corresponding subset of the second plurality of wires 208. The fourth plurality of electrodes 241 form a utricular vestibular nerve branch electrode array 242 such that the fourth plurality of electrodes 241 are held substantially fixed with respect to each other. The electrical lead 200 also includes a fifth plurality of wires 251 and a fifth plurality of electrodes 252 (also not individually illustrated in FIG. 3) that are in electrical contact with a corresponding subset of the third plurality of wires 214. The fifth plurality of electrodes 251 form a saccular vestibular nerve branch electrode array 252 such that the fifth plurality of electrodes 251 are held substantially fixed with respect to each other. The electrical lead 200 also includes a sixth plurality of wires 261 and a sixth plurality of electrodes 262 (also not individually illustrated in FIG. 3) that are in electrical contact with a corresponding subset of pins from the connector. The sixth plurality of electrodes 261 form a cochlear nerve branch electrode array 262 such that the sixth plurality of electrodes 261 are held substantially fixed with respect to each other. The term substantially fixed is intended to include embodiments in which the first 204, second 210 and third 216 pluralities of electrodes are encased or otherwise incorporated in a flexible structure, such as a polymer material. The electrical lead 200 also includes a reference electrode 220 in electrical connection with a corresponding reference wire 222. The reference electrode 220 can be a near reference, such as a common crus reference electrode according to some embodiments of the current invention. Some embodiments can further include a far reference electrode 224 in electrical connection with a corresponding far reference wire 226. Some embodiment can further include a second set of leads and electrodes extending from the connector, analogous to those described above, for implantation of the opposite ear's vestibular labyrinth.

Figure 4:
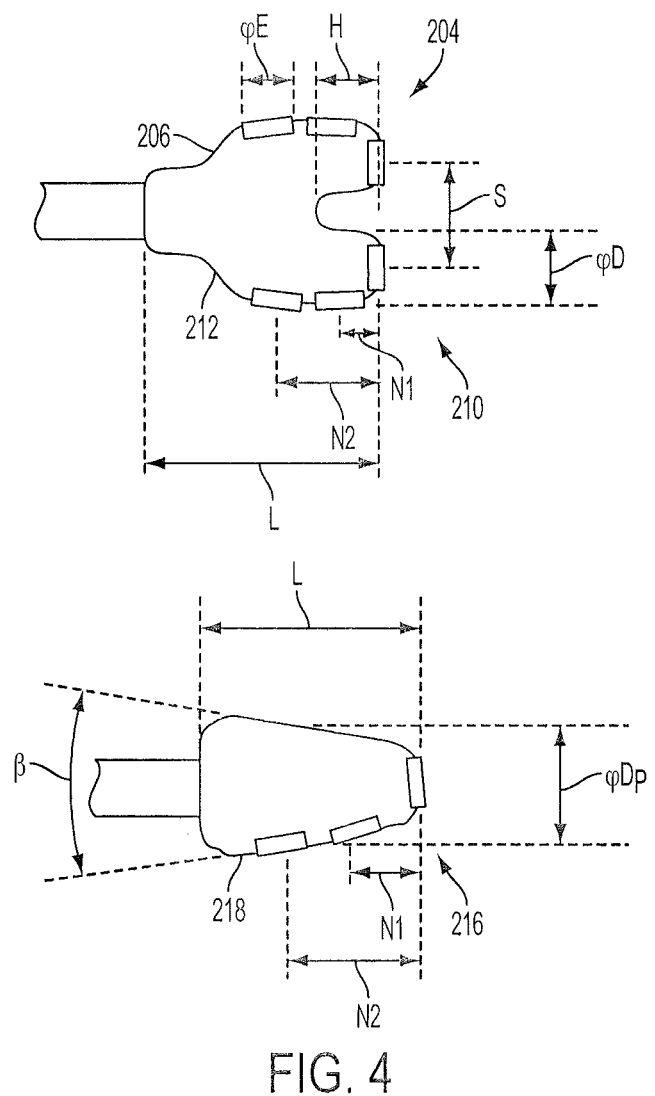
FIG. 4 is a drawing showing an example of HS and P electrode arrays according to an embodiment of the current invention. The dimensions and the position of each electrode contact are based on measurements obtained from computer aided tomography and magnetic resonance imaging scans of a human temporal bone like that shown in FIG. 1: L=2.9 mm, N1=0.725 mm, N2=1.45 mm, H=1.45 mm, S=1.95 mm, $\phi E$=0.5075 mm, $\phi D$=0.5075, $\phi Dp$=0.7975, $\beta$=24°.

The first plurality of wires 202, the second plurality of wires 208, the third plurality of wires 214, the reference wire 222, and the far reference wire 226 can some or all have a device end attached to a common device connector according to some embodiments of the current invention. FIGS. 3 and 4 illustrate an embodiment of an electrical lead 200 for an implantable vestibular stimulation device in which the superior vestibular nerve branch electrode array and the horizontal vestibular nerve branch electrode array are connected such that they remain substantially fixed relative to each other to facilitate simultaneous alignment during surgical implantation. In this example, the superior, horizontal and posterior vestibular nerve branch arrays each have three electrodes and corresponding three wires. In some embodiments, the electrode leads 204, 210, 216, and 220 include a kink, bend, bump, bulge and/or marker to prevent overinsertion. Dimensional parameters that were found suitable for use in people are also provided above. However, the general concepts of the current invention are not limited to this particular example.

Figure 5:
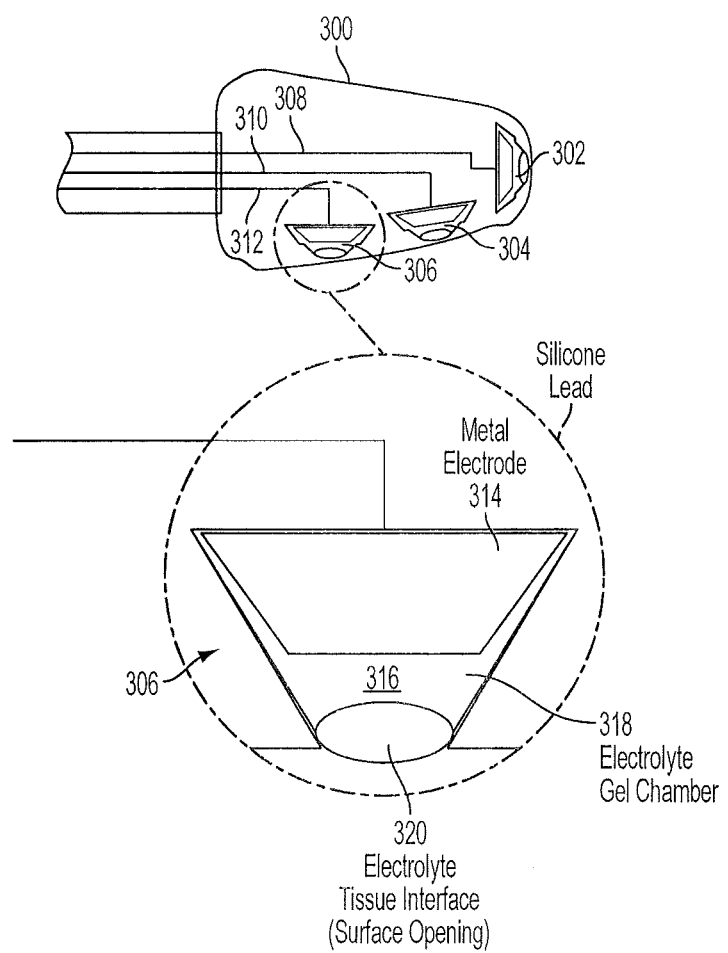
FIG. 5 illustrates an example of chamber electrodes according to an embodiment of the current invention. A conic electrode design allows a large surface area metal electrode to be in contact with the electrolyte to allow large stimulation currents without causing undesirable irreversible electrochemical reactions that corrode the electrode and poison nearby tissue, while having a effective small surface area and therefore high current density field for more precise targeting and more intense stimulation of the nerve. The chamber is filled with electrolyte (either saline or a similarly conductive liquid, gel or solid), which conducts the current from the metal electrode to the targeted tissue.

FIG. 5 illustrates an embodiment of an electrode array 300 that has a plurality of electrodes 302, 304, and 306 and corresponding wires 308, 310 and 312. This is an example in which the electrodes 302, 304 and 306 are chamber electrodes. For example, the chamber electrode 306 includes a metal electrode 314 and an electrolyte gel 316 within a gel chamber 318. The gel chamber 318 defines an opening 320 for electrical contact with tissue. Any one, plurality or all of the electrodes of the electrical lead 200 can be chamber electrodes according to some embodiments of the current invention.

An alternate embodiment of the chamber electrode can have the saline/gel conductor chamber extend back up along the wire lead some distance so as to allow creation of a device without a metal electrode pad 314 being large compared to the dimensions of the carrier 300. Another embodiment can use flat cables as conductors 310, 312 to increase the area of the metal/saline interface. The chamber can assume any shape that connects a relatively larger area metal-saline interface to a relatively smaller pore in the insulating carrier from which the chamber is excavated or otherwise formed. The metal electrode can be a rectangular pad as shown in this embodiment, but can assume any shape, including a wire or flat metal conductor as is typical of photolithographic patterning. The particular metals, insulators and ionic conductive media may differ from the Pt/Ir, silicone and saline gel in this embodiment.

Example

Electrical Lead

The electrical lead 200 can aid in systematic surgical placement of stimulation contacts close to each of the stimulation sites with two possible choices for electrical reference to allow further control the path of the stimulation current. The selection of one of the three electrodes for each stimulation site along with a choice of one of two reference electrodes can aids in faster and more reliable electrode placement and postsurgical selection of the stimulating and reference electrodes to more optimally target each stimulation site, for example.

The electrical lead 200 can include a percutaneous connector, two reference electrodes (Far and Near), and two stimulation leads (P and HS) which have the electrode contacts strategically positioned to be implanted near each of the branches of the vestibular nerve (FIG. 3).

The connector contains 11 pins in the illustrated embodiment for connecting the prosthesis to the electrode. The pins connect with a separate PtIr wire to each of the PtIr electrode contacts on the P (3 contacts) and HS (6 contacts) leads, and the two reference electrodes. The entire array is composed of flexible medical grade silicone with the PtIr wires running inside the silicone from the connector to each of the electrode contacts. The wires are coiled inside the silicone along the length of the electrode to provide stress relief during stretching and bending of the leads. This construction is similar to the standard electrode construction typically employed during manufacturing of cochlear implant arrays.

The HS lead contains six electrode contacts—three electrodes target the horizontal branch of the vestibular nerve, and three other electrode contacts target the superior branch of the nerve. The P lead also contains three electrode contacts. Having multiple contacts allows the option of choosing the electrode contact on each lead which would provide the most selective stimulation of each of the nerve branches (FIG. 4).

Figure 1:
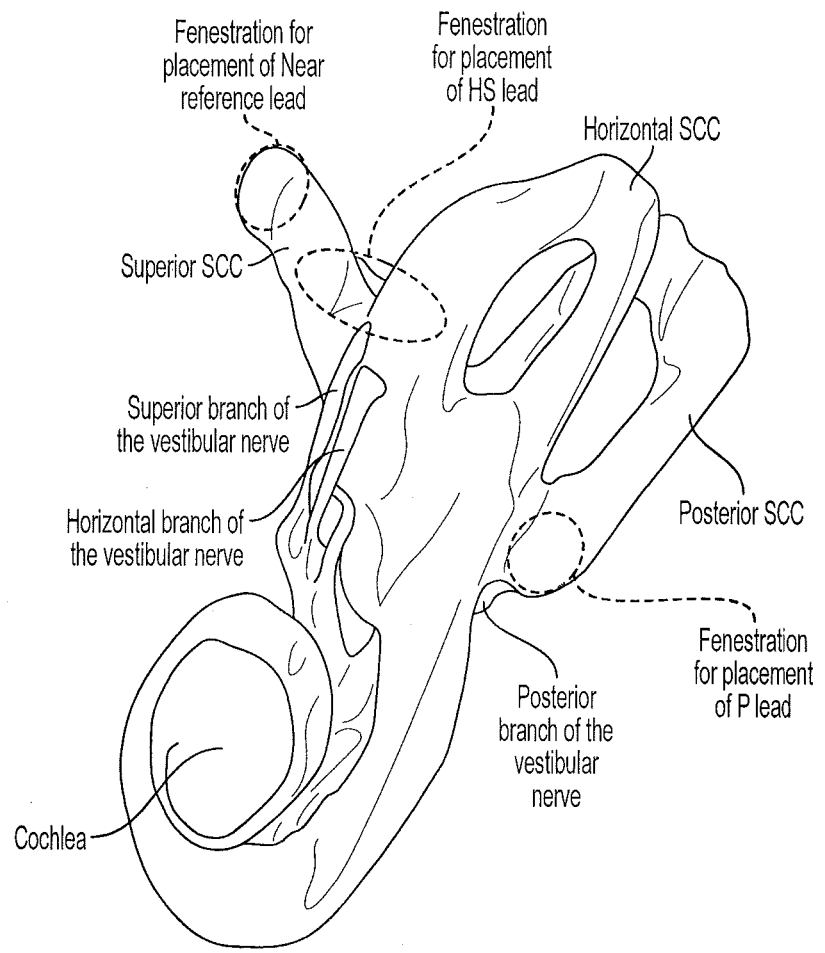
FIG. 1 shows an anatomical model of the inner ear and the vestibular nerve obtained from 3D reconstruction using computer-aided tomographic and magnetic imaging scans of the human temporal bone. The labyrinth is shown approximately as it would be oriented during the surgical approach. The locations of the surgical insertion according to an embodiment of the current invention of the horizontal/superior (HS) lead, the posterior (P) lead, and the "near" reference are shown in dashed ovals.

The conventional stimulation paradigm commonly employed in cochlear implants, delivers monopolar stimulation from an individual electrode contact to the muscle reference (Far reference). This stimulation method, if used by the vestibular prosthesis can result in unintended activation of the facial nerve, which runs parallel to the vestibular nerve in the temporal bone. In this case, it would be desirable to have an alternative stimulation methodology, which would not unintentionally target the facial nerve. To provide an alternative electrical current return, the "near" reference is intended to be inserted into the common crus of the vestibular labyrinth via a fenestration in the superior SCC (FIG. 1). Stimulation with respect to the near reference rather than the "far" reference has the potential of keeping the electrical current path primarily internal to the SCCs, thus lowering the possibility of the electrical current unintentionally exciting the facial nerve. Using the near stimulation reference may however come at the cost of reduced stimulation selectivity and increased stimulation threshold as compared to using the far reference. To allow the choice between using the two references, both reference electrodes are provided on the array.

The additional benefit of having multiple electrode contacts on each of the leads of the array at a variety of locations is that bipolar and multipolar stimulation paradigms can be used here to provide further options for more selective targeting of each of the branches of the nerve. Using multipolar stimulation allows the electrical current to flow not just from an individual electrode to the near or far reference, as in monopolar stimulation, but also to any other electrode or combination of electrodes.

This design uses a large surface area electrode that is contained inside the insulating lead. The electrode conducts current to the electrolyte that is contained inside a conical chamber, with a constricted opening at the surface of the lead. This design allows larger currents to flow safely because the surface area of the electrode can remain large, while targeting a smaller neural population because the port hole can remain small.

Figure 6:
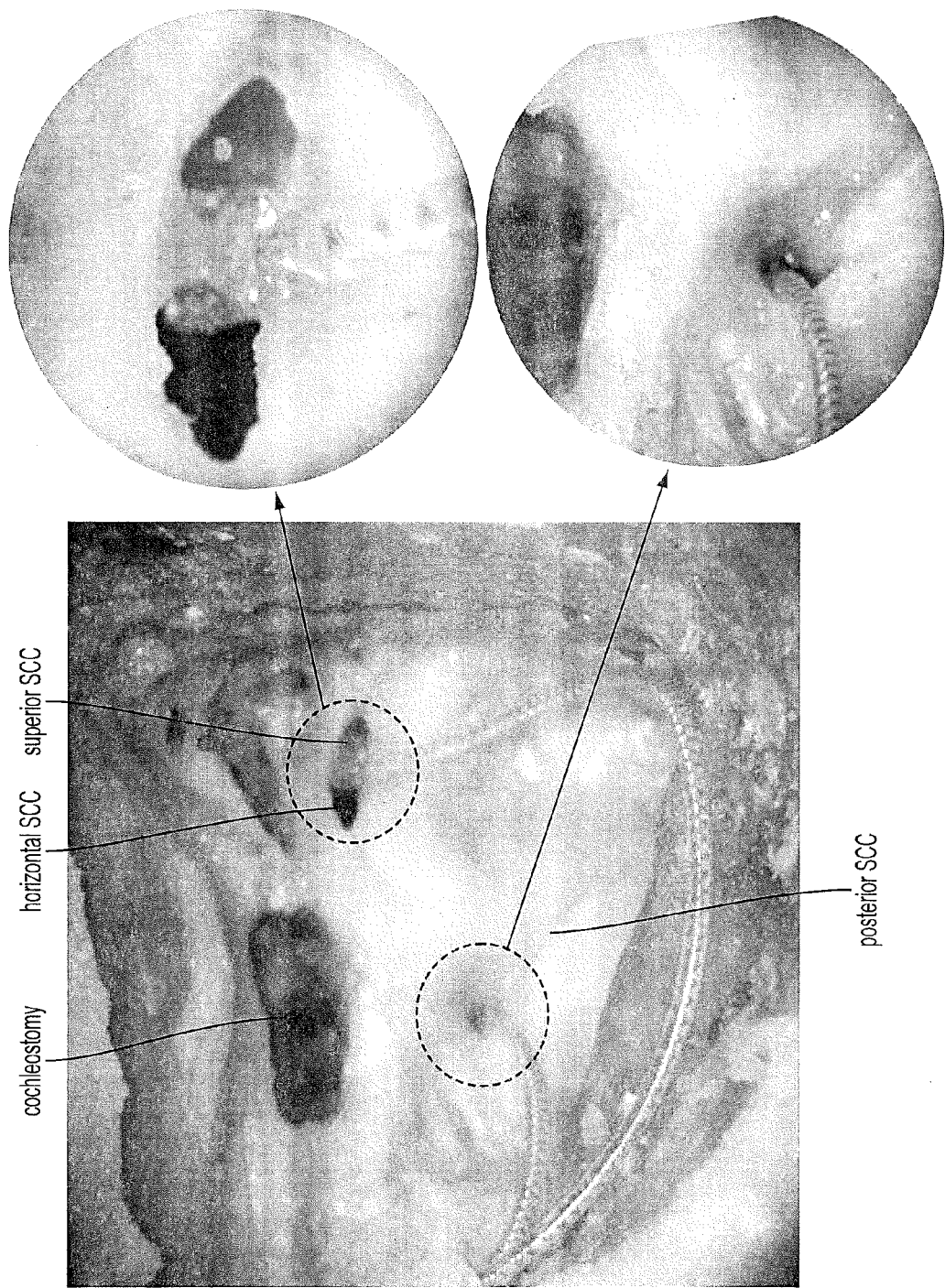
FIG. 6 shows the surgical insertion of HS and P electrode leads according to an embodiment of the current invention in a temporal bone.

Several prototypes of the electrode array have been built according to the prescribed specifications. The prototypes were first tested for surgical placement in a temporal bone (FIG. 6). The size and shape of the HS and P leads were indeed helpful during the surgical positioning of the electrode.

Further enhancements on this electrode may include positioning of an insulating partition (silicone or fat or other material) in the HS electrode to separate the electrodes intended to stimulate the horizontal and the superior branches of the nerve. Additionally, this electrode could be coupled with a cochlear implant electrode to provide the ability to implant a prosthesis which would have the capability of both a cochlear and a vestibular implant for patients who suffer from sensorineural loss of both vestibular and auditory function.

Example

Alignment correction

The vestibular labyrinth in each ear senses angular velocity about each of three orthogonal axes, commonly referred to by their anatomical orientation as Horizontal (H), Left-Anterior-Right-Posterior (LARP), and Right-Anterior-Left-Posterior (RALP). Vestibular prostheses contain orthogonally oriented gyroscopes to sense angular velocity. Commercially available gyroscopes are packaged together in a single integrated circuit, e.g. IGT3200 from InvenSense. This package can be positioned on the circuit board of a vestibular prosthesis according to an embodiment of the current invention. During surgical implantation of the vestibular prosthesis, the ideal positioning of the prosthesis would be such as to align the axes of the gyroscopes on the circuit board with those of the normal labyrinth. This would however impose a rather stringent requirement on the surgeon given the anatomical variability between patients and more immediate stressful concerns encountered during surgery. For this reason it is necessary to find out the orientation of the gyroscopes relative to the labyrinth orientation after the surgical implantation. Once the orientation of the gyroscopes relative to the head is known, a linear coordinate transformation can be performed to algorithmically align the gyroscope orientation with vestibular labyrinth. An embodiment of the current invention provides a way to obtain the orientation of the prosthesis relative to the orientation of the vestibular labyrinth to obtain a transformation matrix M that can then be used with a linear coordinate transformation algorithm.

To accomplish this we add accelerometers to the vestibular prosthesis. Commercially available 3D accelerometers (e.g. LIS331DL from STMicro) are packaged together in the same integrated circuit, and likely will be packaged together with the gyroscopes in the near future (e.g. MPU-6000 from InvenSense). The individual axes of the accelerometer are positioned on the prosthesis circuit board to align with the axes of the gyroscopes.

During the post-surgical fitting procedure, the person's head is positioned consecutively to align along each of the three vestibular labyrinthine axes (H, LARP, and RALP). During each of the positions, the accelerometer reading provides the acceleration due to gravity measured by its X, Y, and Z components.

Figure 7:
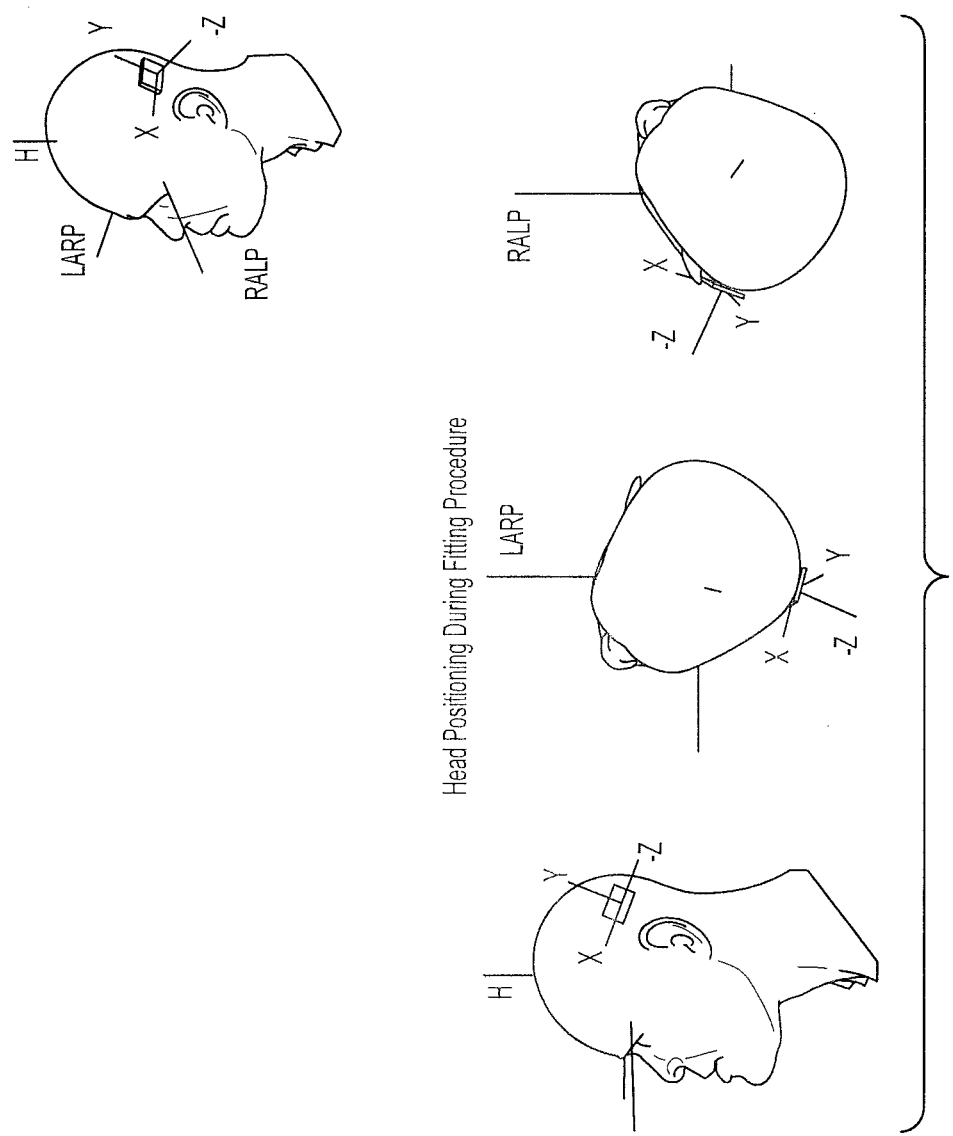
FIG. 7 is a schematic illustration to explain alignment corrections according to an embodiment of the current invention. The definition of head and prosthesis coordinate frames are shown in the top right panel, and head orientations for fitting the prosthesis to align the sensors to the head centered reference frame are shown in the lower three panels.

FIG. 7 shows the approximate alignment of the circuit board with respect to the head and the relationship between the head centered coordinate frame (indicated by H, LARP, and RALP) and the prosthesis centered coordinate frame (indicated by X, Y, Z) after implantation.

In the ideal surgical placement, the prosthesis axis Y in FIG. 7 will align with the H axis of the head, Z axis would align with the LARP axis, and X would align with RALP axis. However, since the surgical placement is subject to error, the circuit board position in FIG. 7 shows a misalignment between the two coordinate frames. We refer to vector $\bar{v}_i$ in head centered coordinate frame in terms of $$\begin{bmatrix} RALP \\ LARP \\ H \end{bmatrix}.$$

Vector $\bar{\alpha}_i$ in prosthesis coordinate frame is described in terms of $$\begin{bmatrix} X \\ YZ \\ ZY \end{bmatrix}.$$

Because the accelerometer measures acceleration due to gravity, when the head is stationary, the vector recorded from the device will be in m/s² and pointing toward ground. In order to remove the dependence on measurement units and account for the accelerometer measurement in the opposite direction of the upward head orientation we normalize and negate the accelerometer measurement:

$$\hat{\alpha}_i = -\frac{\bar{\alpha}_i}{\|\bar{\alpha}_i\|}$$

for each of the three head positions i.

The relationship between the vector $\hat{\alpha}_i$ to the corresponding vector in the head coordinate frame $\bar{v}_i$ is $\hat{\alpha}_i = M\bar{v}_i$, where M is a 3×3 matrix. The fitting procedure calls for recording the accelerometer vector $\hat{\alpha}_i$ in each head orientation. Once the three accelerometer values have been recorded we find the coordinate transformation matrix M by solving the system of equations:

$$\hat{\alpha}_{RALP} = M\begin{bmatrix} 1 \\ 0 \\ 0 \end{bmatrix}, \hat{\alpha}_{LARP} = M\begin{bmatrix} 0 \\ 1 \\ 0 \end{bmatrix}, \hat{\alpha}_H = M\begin{bmatrix} 0 \\ 0 \\ 1 \end{bmatrix}$$

The particular selection of the head orientations simplifies the transformation matrix to the columns composed of the accelerometer vectors: $M = [\hat{\alpha}_{RALP}\ \hat{\alpha}_{LARP}\ \hat{\alpha}_H]$.

Standard linear algebraic methods can be used to perform the calculations to correct for gyroscope alignment in real time by using the inverse of the transform matrix, $G_i = M^{-1} g_i$, where $g_i$ is the gyroscope measurement on the prosthesis and $G_i$ is the corresponding rotation in head-centered coordinates. Matrix M can be inverted because it describes the rotational relationship between two orthonormal coordinate frames.

Example

Linear Compensation for Channel Interaction

We can correct for stimulation channel interaction by applying linear coordinate transformation between the coordinate system described by the head centered reference frame and the reference frame described by the perceived axis of motion due to stimulation delivered to each of the three electrodes.

The concept of linear coordinate transformation is a standard tool described in the fundamental linear algebra textbooks. According to an embodiment of the current invention, we can use same linear algebra mathematical techniques to provide a novel correction for electrical stimulation channel interaction in prostheses. We realign the perceived head motion resulting from electrical stimulation, which may have inaccuracies due to current spread inherent in electrical stimulation, with the actual head motion as sensed by the gyroscopes.

According to this embodiment of the current invention, we stimulate with each of 3 channels of prosthetic stimuli, measure the eye movement response directions, which are indicative of the net effect of current spread, and then back-calculate the linear coordinate transformation of sensor inputs required to achieve well-aligned eye responses.

In theory, one should be able to overcome the effects of current spread from an electrode targeting one ampullary nerve by adjusting the input delivered via other electrodes targeting two other ampullary nerves in the same (or contralateral) labyrinth. For example, if current intended for the horizontal ampullary nerve spuriously excites the anterior and posterior ampullary nerves, then head rotation purely about the horizontal semicircular canal (SCC) axis might be encoded by modulating not only the horizontal electrode input, but by simultaneously modulating stimuli on all 3 electrodes to represent a horizontal head rotation via vector summation. If linearity and vector superposition hold, this procedure amounts to a simple linear transformation between two different 3D coordinate systems. One characterizes this transformation by delivering a set of stimuli $\bar{s}_i$ (with each $\bar{s}_i$ a 3-vector representing a triplet of stimulus intensities delivered via 3 electrodes targeting the 3 ampullary nerves) and measuring the corresponding responses $\bar{r}_i$ (with each $\bar{r}_i$ a 3-vector representing the axis and speed of observed eye movement responses) for a set of N virtual head movements spanning the range of head movement axes and rotational velocities normally encoded by the labyrinth. A single 3×3 matrix R can then be found using least-squares techniques such that $$\bar{r}_i \approx R\bar{s}_i \text{ for } i=1 \ldots N \tag{1}$$

Once R has been established, the appropriate pattern of electrode activation $\bar{a}$ the prosthesis should deliver to the 3 ampullary nerve electrodes during a head rotation eliciting gyroscope signals $\bar{g}$ is $$\bar{a} = R^{-1}\bar{g} \tag{2}$$

This procedure requires that R is computed during an occasional "fitting" session, analogous to fitting required for patients with cochlear implants. For this procedure to work properly, the axes of eye movement responses to individual stimulation of each the 3 ampullary nerves must be linearly independent with respect to each other. Otherwise, the inverse of R does not exist and the matrix pseudoinverse calculation will fail. In this context, linear independence means that the 3D axis of angular vestibular ocular reflex (VOR) responses to stimuli delivered via any one electrode alone cannot be in the plane defined by the axes of responses to the other two electrodes. The accuracy with which linear precompensation can correct for current spread also depends on the extent to which the electrically-evoked VOR response is linear and obeys vector summation.

Fitting Procedure for Linear Compensation

The following fitting methodology can be used in order to find matrix R. In this method for fitting the prosthesis we generate signals by a computer to substitute the signals normally delivered by the gyroscopes that sense head rotation. This method emulates head motion input to the vestibular prosthesis without having to physically move the head of the patient. The VOR eye response to vestibular prosthesis stimulation are assayed using standard VOR measuring techniques, such as videooculography (VOG) or scleral search coil technique.

During the fitting procedure we first set the amplitude of the current pulses delivered to each electrode. The amplitude of the pulses delivered to each electrode is determined by slowly increasing the current level of the stimulation while modulating the frequency of the stimulation periodically between low and high pulse rates to elicit VOR, for example, 0 and 400 pulses per second (pps) at 2 Hz. At threshold amplitude, the VOR eye response causes the eyes to start moving back and forth at, for example, 2 Hz about an axis that is appropriate to the branch of the vestibular nerve that receives stimulation. The eye velocity increases with amplitude. We increase the amplitude of the pulses until the stimulation current starts to spread to other branches of the vestibular nerve indicated by the change in axis of eye response, or when the patient experiences facial stimulation in form of muscle twitch. The target amplitude is recorded at just below this stimulation level. This procedure is conducted for each of the three electrodes implanted near the corresponding (LARP, RALP, and Horizontal) branches of the vestibular nerve.

Figure 8:
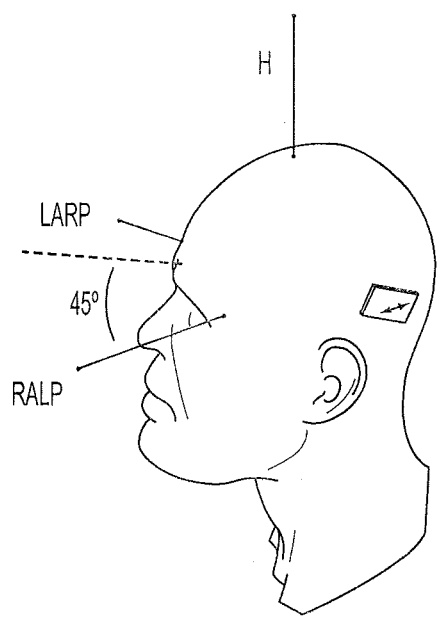
FIG. 8 is a diagram of a head centered coordinate frame represented by the LARP, RALP, and H cardinal axes and roll axis of motion indicated using a dashed line. The prosthesis is shown as a square and the gyroscopes are assumed to be aligned with the head centered coordinate frame.

Assuming the gyroscopes were aligned with the head centered coordinate system (either surgically or algorithmically as described above), if the head were to be rotated back and forth about a given axis, the gyroscope signals encoding the velocity of this motion would be sinusoidal with the same frequency but differing in amplitude. The amplitude of the sinusoidal signal reported by each gyroscope would correspond to the relative contribution of head motion about the axis encoded the gyroscope. For example, if the head were to rotate back and forth sinusoidally at 50 deg/s peak velocity at 2 Hz about the yaw axis, the gyroscope encoding motion about that axis (H) would oscillate at 2 Hz between −50 deg/s and 50 deg/s and the other two gyroscopes would report 0 deg/s. Alternatively, if the head were to sinusoidally rotate back and forth about the roll axis shown in FIG. 8 with a dashed line (at 45 deg from the LARP and RALP axes about an axis positioned along the horizontal plane), the horizontal gyroscope would not modulate at all, but the LARP and RALP gyros would each modulate sinusoidally at 2 Hz between $$+50\left(\frac{1}{\sqrt{2}}\right) \text{ and } -50\left(\frac{1}{\sqrt{2}}\right) deg/s.$$

To emulate the gyroscope encoding of the sinusoidal head motion about any axis, we deliver the corresponding sinusoidal signals simultaneously to each gyroscope at a given frequency of oscillation with the amplitude of the modulation corresponding to the relative contribution of each gyroscope. The stimulation vector $\bar{s}_i$ representing this motion is composed of the amplitude of the sinusoidal component as if it were sensed by each gyroscope $$\begin{bmatrix} RALP \\ LARP \\ H \end{bmatrix}.$$

In the examples mentioned above, the 50 deg/s motion about the yaw axis will be specified by $$s = \begin{bmatrix} 0 \\ 0 \\ 50 \end{bmatrix}$$

while the rotation about the roll axis will be specified by $$s = \begin{bmatrix} 35,35 \\ 35,35 \\ 0 \end{bmatrix}.$$

For each stimulation vector $\bar{s}_i$ we record the eye velocity vector $\bar{r}_i$ also in the same head coordinate system. In this way we obtain the eye responses to the N rotations spanning the space of possible head rotations at different velocities and orientations. Once these N stimulus-response pairs have been obtained we use standard linear least squares estimation to obtain matrix R which maps the stimulus to response pairs, such that $\bar{r}_i \approx R\bar{s}_i$.

Example

Implantable Vestibular Stimulation Device

An embodiment of the current invention is directed to a new generation vestibular prosthesis. A prototype (here denoted the MVP2) has been developed, which addresses many of the limitations of previous devices. The new device occupies less space, consumes less power, measures 3D rotation and linear acceleration, delivers multipolar stimuli via multiple independent current sources, and incorporates circuitry for wireless control and in situ measurement of electrode impedances.

Device Description

System Design

Figure 9:
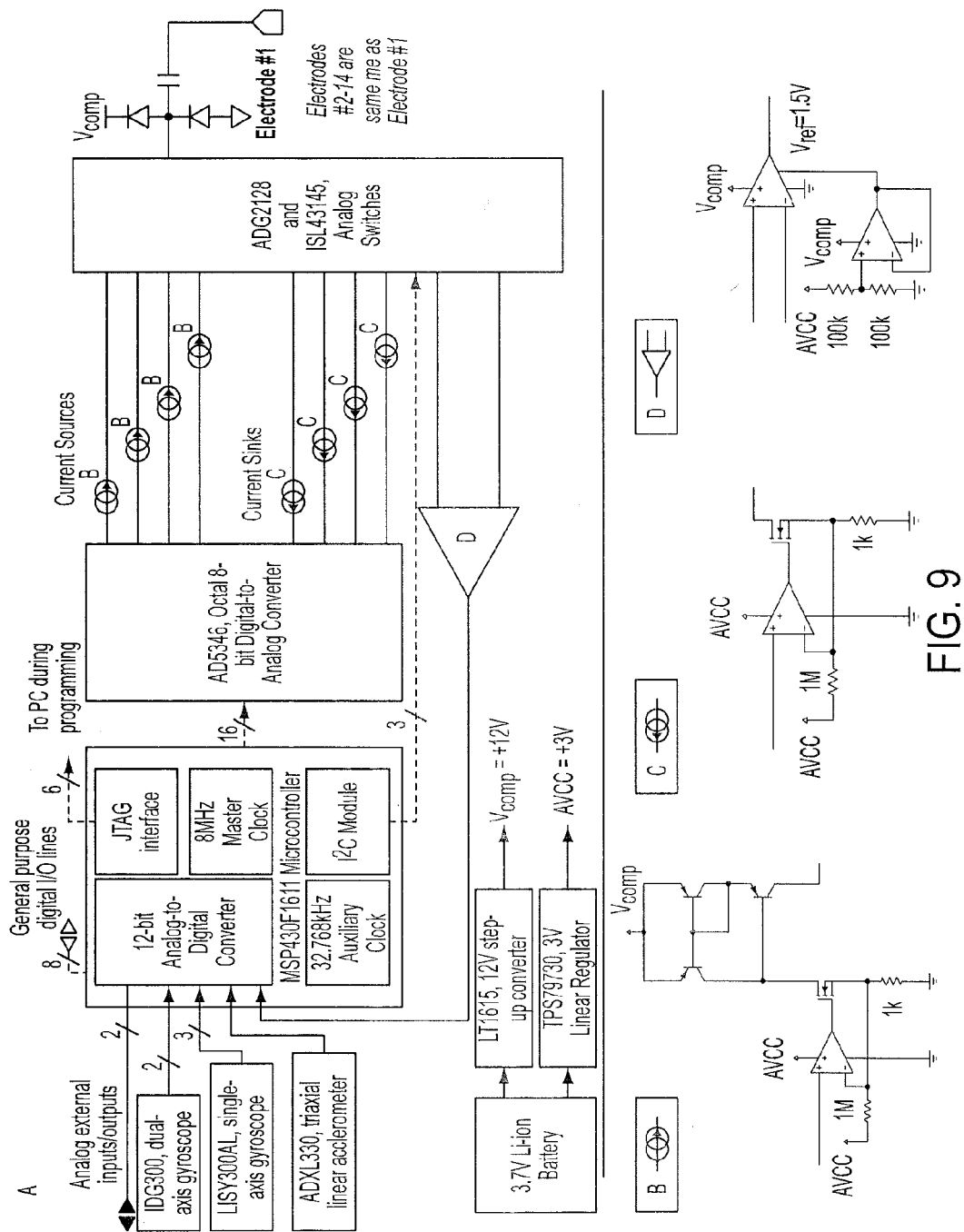
FIG. 9 is a schematic diagram of an implantable vestibular stimulation device according to an embodiment of the current invention. Panel A summarizes the circuitry of the implant. The sensors, on the left, are read into the microcontroller's 12-bit Analog-to-Digital Converter (ADC) every 10 ms. The microcontroller performs calculations to determine the instantaneous rate at which pulse-frequency-modulated biphasic charge-balanced pulses are delivered. Each pulse is performed by commanding the eight independent current sources via the Digital-to-Analog Converter (DAC) and toggling the analog switch lines to the 13 electrodes on the right. An onboard amplifier, for use measuring electrode impedance, can be connected to any of the electrodes and its output can be read by the ADC of the microcontroller. Two power supplies, +3V and +12V, are drawn from a single-cell 3.7V Li-ion battery. Panels B, C, and D demonstrate the circuitry of the high-side voltage-controlled current source, voltage-controlled current sink, and amplifier, respectively. Gray lines represent digital signals while black lines represent analog signals.

FIG. 9 is a schematic illustration of an example of an implantable vestibular stimulation device according to an embodiment of the current invention, which we will refer to as MVP2. The MVP2 detects motion using MEMS gyroscopes and linear accelerometers. All sensor outputs are simultaneously sampled every 10 msec by a microcontroller, which controls timing of stimulus pulse trains delivered via an array of electrodes switched dynamically via software control. Each pulse is biphasic and charge-balanced, with current amplitudes of 0 to 1 mA (resolution 4 µA) per stimulation unit and pulse durations of 25 µs to 1000 µs (resolution 0.125 µs). The microcontroller controls 4 current sources and an analog switching network and that can route stimulus currents through any four anodic electrodes to any four cathodic electrodes, allowing simultaneous stimulation on up to four bipolar electrode pairs. A total of 13 electrodes are available, allowing connection as twelve monopolar electrodes with respect to a distant reference, or six bipolar pairs, or different tripolar or quadripolar configurations. When activated, an onboard sense amplifier measures the voltage potential across any two groups of electrodes, a function required for in situ self-testing of electrode impedance and measurement of evoked neural potentials. Each module of the system is described in greater detail in the following sections.

Sensors

Figure 10:
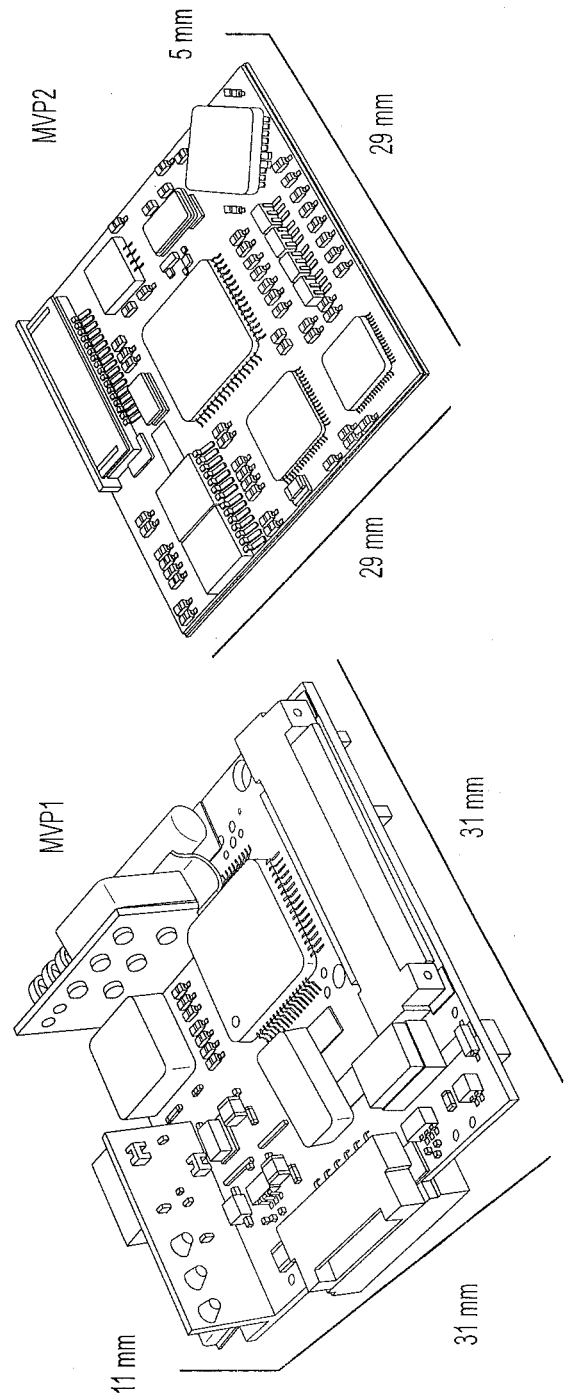
FIG. 10 shows side-by-side views of a multichannel vestibular prosthesis (MVP2, right) according to an embodiment of the current invention and the original multichannel vestibular prosthesis (MVP1, left). Using a now-available dual-axis gyroscope, the height of the MVP2 is less than half that of MVP1, which had to use two single-axis gyroscopes mounted on edge to sense in 3D. The dual-axis gyroscope of the MVP2 is rotated 45° on the plane of the board so that the MVP2 senses in the horizontal, LARP, and RALP rotational axes and the naso-occipital, interaural, and parasagittal translational axes.

For detecting 3D rotational velocities, the MVP2 uses a yaw-axis angular rate sensor (LISY300AL, STMicroelectronics, Geneva, Switzerland) and a dual-axis roll/pitch gyroscope (IDG300, InvenSense, Sunnyvale, Calif.). A triaxial linear accelerometer (ADXL330, Analog Devices, Norwood, Mass.) senses 3D translational acceleration. As pictured in FIG. 10, the IDG300 dual-axis angular rate sensor is positioned flush on the board but is offset 45° from the ADXL330 so that when the latter is aligned with the anteroposterior (X, +nasal), interaural (Y, +left) and superoinferior (Z, +up) head axes, the gyro directly senses rotations aligned approximately with the axes of the LARP and RALP SCC's. Sensors used in the MVP2 afford a significant improvement in size, capability and power consumption compared to the MVP1 (Table 1). MVP2 total sensor power consumption is 44 mW, less than 50% of the MVP1's 3 single-axis gyros (90 mW). This reduction in power consumption is achieved despite the addition of triaxis linear acceleration sensing and a reduction in overall circuit thickness to 5.3 mm, a reduction to less than 50% of the MVP1 thickness (mainly due to replacing the two single-axis gyroscopes that had to be mounted on upright daughter boards in the MVP1).

TABLE 1

Sensor Characteristics

| Name | Zero-Rate Value (V) | Resolution | Total Range | Voltage (V)/Current (mA) |
|---|---|---|---|---|
| ST LISY300AL | 1.65 | 3.3 mV/°/s | ±300°/s | 3.0 V/4.8 mA |
| InvenSense IDG300 | 1.5 | 2.0 mV/°/s | ±500°/s | 3.0 V/9.5 mA |
| Analog Devices ADXL330 | 1.5 | 300 mV/g | ±3.6 g | 3.0 V/0.32 mA |
| Analog Devices ADXRS300 | 2.5 | 5.0 mV/°/s | ±300°/s | 5.0 V/6 mA |

Processor

The MVP2's microcontroller (MSP430F1611, Texas Instruments, Austin, Tex.) is clocked by an 8-MHz crystal. In addition to sampling sensor signals, controlling stimulus pulse timing, and sampling a sense amplifier to measure potentials across electrodes, it can communicate via a wireless serial connection to a separate laptop running a graphical user interface for adjustment of stimulus parameters. The processor incorporates a 16-bit RISC architecture with 10-kB of RAM, 48-kB of flash memory, eight 12-bit analog-digital converters, flexible timing mechanisms, low power modes, and two serial communication interfaces (UART and I$^2$C) in a small package (9×9×1 mm$^3$). The analog-digital converters are used to sample gyroscope, accelerometer, and potential differences between any two electrodes. The timer module provides up to seven independent timers operating at 32,768 Hz (all of which schedule ADC sampling and control pulse-rate timings in the MVP2) and three timers operating at 8 MHz (to control fine timing of biphasic current pulses). To deliver a stimulation pulse, the microcontroller first sets the amplitude of a voltage-controlled current source and then defines the active electrodes via I$^2$C commands to a crosspoint switch array. Between stimulus pulse transitions, the microcontroller is toggled to a low-power mode in which it consumes 330 µA to retain memory and drive the crystals/timers in between events; when fully active, it draws 4 mA from a 3V regulated supply.

Current Source and Switching

The MVP2 can control current amplitudes on up to four electrodes supplying the current (termed current sources) and up to four other electrodes sinking the current (termed current sinks). The four current sources and four current sinks are multiplexed through analog switches (ADG2128-HS, Analog Devices, Norwood, Mass. and ISL43145, Milpitas, Calif.), under the microcontroller's control, to any combination of the thirteen electrodes. The second phase of each biphasic pulse is created by simply swapping the current sources and current sinks used to create the first pulse phase for any given bipolar pair or multipolar group of electrodes. In addition, the ADG2128-HS has the ability to connect any pair of electrodes to the sense amplifier's input.

An octal digital-to-analog converter (AD5346) sets voltages that indicate the desired current for each of 4 anode-side current sources (FIG. 9, Panel B) and 4 cathode-side current sinks (FIG. 9, Panel C). All current sources and sinks can control current amplitudes in the range of 0 to 1 mA with a resolution of 3.9 µA. A compliance voltage of +12 V ensures that current sources can deliver desired current through each electrode pair's typical ~20-40 kΩ series impedance.

Electrode Potential Amplifier

The electrode potential amplifier (EPA) is comprised of one stage of an instrumentation amplifier (AD8224) (FIG. 9, Panel D). The two inputs into the amplifier can be connected to any electrode pair through the crosspoint switch network. An amplifier gain of ⅛ and output DC offset of 1.5 V are used to ensure that the maximum biphasic pulse amplitude possible (24V differential) can be directed into the microcontroller's analog inputs without causing damage. EPA output sampled at up to 200-kSamples/s by the microcontroller can be transmitted to an external laptop for display and analysis.

Software

We program the microcontroller using the Embedded Workbench by IAR Systems AB (Uppsala, Sweden), and a flash emulation tool through the microcontroller's JTAG interface. The normal function of the MVP2 is dictated by three timer-driven interrupt service routines: (1) a Parameter-Set routine allowing in situ adjustment of device parameters via the user interface; (2) a Fine-timing routine to generate each biphasic pulse; and (3) a Sample/Update routine to update each stimulus channel's pulse rate based on motion sensor inputs.

The Sample/Update routine runs every 10 ms. It enables simultaneous analog/digital conversion (ADC) for all motion sensor channels, optionally preprocesses raw signals via time-domain filtering, corrects for sensor/response misalignment with a coordinate transformation, and updates pulse frequency accordingly for each gyro channel using a 12-bit resolution head-velocity-to-pulse-rate mapping between angular velocity (over interval −300 to +300°/s) and pulse rate (over interval 0 to 400 pulse/sec) similar to that previously described for MVP1. This mapping defines a piecewise-linear relationship, with a species-specific baseline rate equal to or slightly higher than the mean normal spontaneous discharge rate for vestibular afferent fibers (e.g., we typically use 60 pulse/s for chinchillas and 94 pulse/s for rhesus macaque monkeys). A look-up table approach is employed to facilitate efficient real time calculation of this nonlinear mapping function. The full range of the 12-bit ADC value is partitioned into 32 bins, each with a slope and intercept defining one segment a piecewise-linear approximation to the nonlinear mapping. The size of this table represents a compromise between memory use and computational time. Using six tables (one for each motion sensor input) occupies 768 bytes of flash memory and requires 222 µs to update the "time-until-next-pulse" for each of six channels.

Electrode Array

Unlike the MVP1, for which electrodes were fashioned from twisted pairs of wires that were difficult to place individually near each SCC's ampullary nerve via standard microsurgical techniques, electrode arrays designed and fabricated for the MVP2 are much more like those of cochlear implants in clinical use. Based on species-specific measurements from 3D reconstructions of microCT images of existing temporal bone specimens for normal chinchillas and rhesus macaque monkeys, each electrode array comprises 9 active and 2 reference electrodes, with active electrodes partly embedded within a silicone carrier. All electrode pads are 90/10 Platinum/Iridium to ensure biocompatibility.

The new electrode arrays simplify surgical implantation because they allow precise microsurgical placement of 9 active electrodes via manipulation of only two silicone carriers. The silicone carriers are shaped to self-orient within each implanted ampulla so that electrodes rest adjacent to target ampullary nerve endings. Each carrier includes 3 electrodes per ampullary nerve target, and the fixed 400 µm spacing between adjacent electrodes. Multiple electrode contacts per ampullary nerve target enables post-surgical programming of the vestibular prosthesis to account for variability of surgical placement and anatomical differences by providing a choice of the possible stimulation sites to more selectively target each of the branches of the ampullary nerve.

The two reference electrodes allow a choice of references for electrical stimulation delivered to each electrode, further improving the ability to target each nerve by providing alternative paths for the flow of the stimulation current. The first reference electrode is a large surface area electrode at the end of an insulated lead and is typically inserted far from the labyrinth in the neck musculature. One or more near reference contacts each consists of an electrode wire inserted into the interior of the semicircular canals near the common crus of the anterior and posterior SCCs.

The MVP2 crosspoint switch array can connect any of the four cathodic current sources or four anodic current sinks to all electrodes, allowing many possible stimulation paradigms. All active electrodes can be used in a monopolar fashion between a stimulating electrode and one of the reference electrodes, bipolar fashion between neighboring electrodes, or multipolar fashion, which allows combinations of the stimulating and reference electrode contacts to be used to allow for improved targeting of each branch of the nerve.

Benchtop Performance

Under typical use conditions, the MVP2 draws 16.7 mA at 3.7V and can operate for 14 hours on a single-cell lithium-ion rechargeable battery shaped like an AAA battery. The MVP2 uses a low dropout 3 V linear voltage regulator (TPS79730, Texas Instruments, Dallas, Tex.) to produce a constant 3.00 V that powers the motion sensors, microcontroller, DAC, and analog switch network. These components represent at least 88% of the power consumed by the prosthesis. An inductor-based step-up converter (LT1615, Linear Technology, Milpitas, Calif.) generates a +12 V supply that serves as the compliance voltage available to drive current through microelectrodes and tissue.

The MVP2 circuitry is built on two sides of a 6-layer 29×29×5.3 mm$^3$ printed circuit board (FIG. 10) using surface-mount technology. The weight of the completed device without battery or wireless interface circuitry is 3.5 g. As compared to the MVP1, MVP2 is more compact and lighter, mainly due to improved MEMs technology and the use of the thinner ribbon connectors instead of the pin-based connectors used for MVP1.

Experimental Methods for In Vivo Tests

Surgery:

An adult wild-type rhesus macaque (*Macaca mulatta*) was used for all in vivo tests of the updated prosthesis. Surgical procedures were conducted in accordance with a protocol approved by the Johns Hopkins Animal Care and Use Committee.

The electrode array comprises a number of strategically positioned electrode contacts to allow the electrical stimulation to be delivered selectively to each of the three ampullary branches of a vestibular nerve. The shape of the electrode array provides ease of surgical placement of one lead of the electrode array, containing two sets of stimulating electrodes, via a single fenestration for independent stimulation of the two neighboring branches of the vestibular nerve. Another lead of the electrode array with a single set of electrode contacts is designed to be placed in a separate fenestration drilled adjacent to the more distal branch of the nerve. Each of the stimulating sets of electrodes contains multiple PtIr contacts.

Vestibulo-ocular Reflex in response to rotation:

With the surgically implanted animal restrained in an apparatus described previously, we recorded the VOR response to electrical stimuli delivered by the MVP2. We connected the MVP2 to the intralabyrinthine electrodes through a percutaneous connector so we were able to rotate the prosthesis freely without rotating the animal. The prosthesis was rotated in 3D space without turning the animal because its right labyrinth was still healthy and capable of sensing rotation. Eye rotation, which was recorded with a 3D eye coil system at 200 Hz, was calculated with in-house software routines programmed in Labview.

Recording electrode impedances with the onboard amplifier:

The MVP2 is capable of evoking vestibular sensation, as well as simultaneously recording electrode impedances. With the animal restrained in the apparatus, we stimulated between pairs of electrodes and recorded the stimulation pulses with the onboard amplifier. We did this between all the intralabyrinthine electrodes with respect to a large 'distant' electrode implanted in the neck musculature. All stimulation pulses had current amplitudes of 170 µA and pulse durations of 200 µs. Sixteen stimulation pulses were averaged to eliminate noise. After recording the output of the amplifier with a Tektronix TPS2024 digital oscilloscope, we calculated the resistances and capacitances for each of the electrodes using Matlab.

Tripolar Stimulation:

The MVP2 is able to simultaneously control the amount of current passed in one electrode and out two electrodes (termed tripolar stimulation). We hypothesized this technique, called tripolar stimulation, could be used to shape the applied electric field and subsequently be used to better control the direction and amplitude of VOR eye responses. The prosthesis was configured to internally modulate pulse rate based on rotation from −300 deg/s to 300 deg/s at 1 Hz.

In response to stimulation presented between the superior SCC electrode (e6) and the large distant electrode (e10), we measured the VOR eye responses while varying the applied current from 0 µA to 200 µA in 20 µA (10% steps) increments. Likewise, the VOR eye responses were measured while changing the amount of current applied from 0 µA, to 200 µA in 20 µA increments delivered across a horizontal SCC electrode (e7) and large distant electrode (e10).

Tripolar stimulation was performed by varying the percentage of current applied in 20 µA steps by the superior SCC electrode. The remaining current amplitude was applied into the horizontal SCC electrode to ensure 200 µA was delivered. Both superior and horizontal SCC electrodes were with respect to the distant electrode implanted in the neck musculature. In addition to the two monopolar and one tripolar cases, we summed the VOR responses acquired from the two bipolar cases offline to compare with the tripolar case.

Results

Results of the in vitro bench tests and in vivo animal experiments are provided below. In vitro bench tests are provided to demonstrate the pulse frequency modulation of spike trains based on the linear accelerometers. The results of in vivo experiments include assessment of VOR eye responses in rhesus monkeys and exploration of the novel features of the MVP2, including results from tripolar stimulation and electrode impedance of the implanted intralabyrinthine electrode.

Figure 11A:
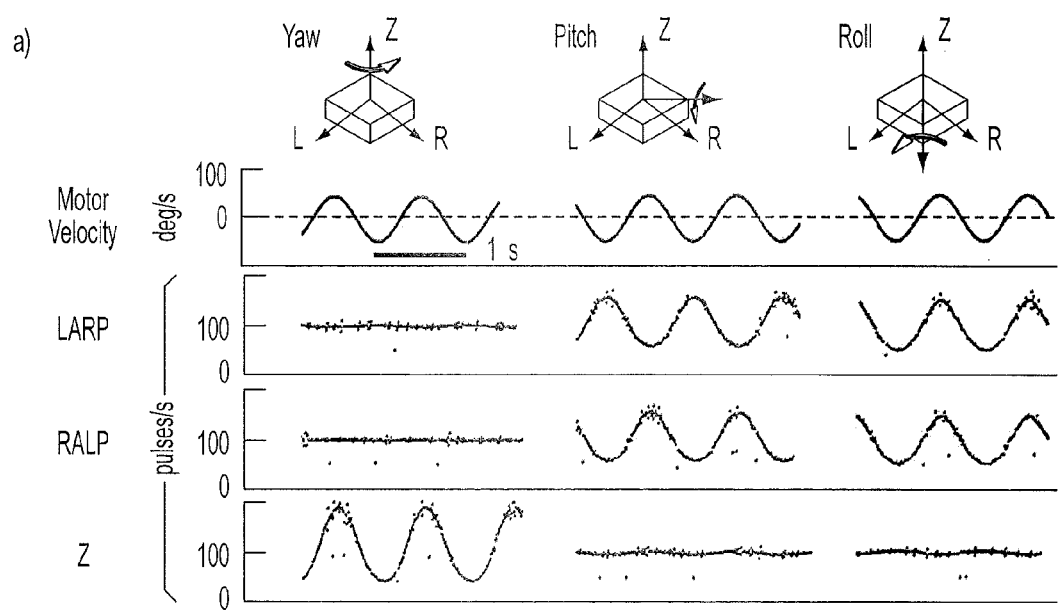
FIGS. 11A and 11B are time plots of pulse frequency modulation by on- and off-axis sinusoidal rotations (FIG. 11A: Pulse Rate Modulation based on Gyroscopic Input.
Figure 11B:
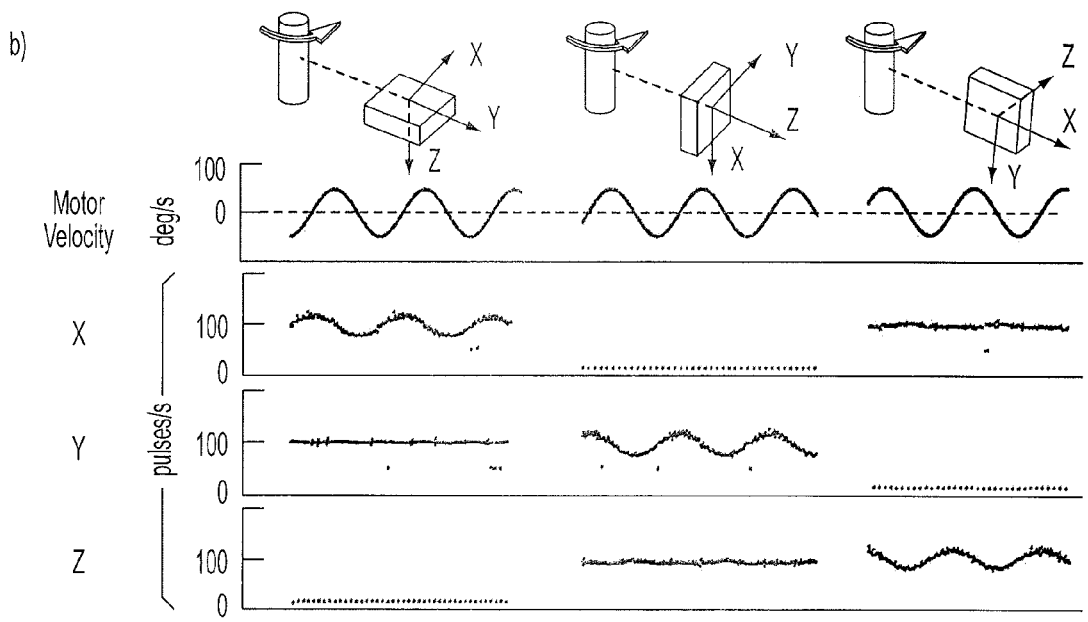

When we tested the pulse frequency modulation driven by the linear accelerometers with sinusoidal motor rotations, we measured an Earth-vertical acceleration with a constant offset (corresponding to a downwards 9.8 m/s$^2$); a sinusoidally-modulated acceleration pointing towards the center of rotation (corresponding to centripetal acceleration); and a sinusoidally-modulated acceleration pointing along the direction of motion (corresponding to tangential acceleration). When a linear accelerometer was aligned with gravitational acceleration (downwards 9.8 m/s$^2$) in the positive direction, the accelerometer input reported a 1.8 V signal which corresponded to a high baseline stimulation rate of ~350 pps (FIG. 11B). In addition, we noted that the sinusoidal centripetal ($a_c$) and tangential ($a_t$) signals were related as expected ($a_c=r\Omega^2$ and $a_t=r(d\Omega/dt)$, where $\Omega$=angular velocity of the motor) (FIG. 11B). As expected, the maximum pulse rate modulated by the tangential accelerometer was ~4 times larger than the maximum pulse rate modulated by the centripetal accelerometer. At 2 Hz, 50°/s sinusoidal rotation with the prosthesis positioned at 20 cm from the center of the motor rotation axis, the movement provides maximal tangential acceleration of 2.08 m/s$^2$, with the maximum centripetal acceleration of 0.14 m/s$^2$.

Figure 12:
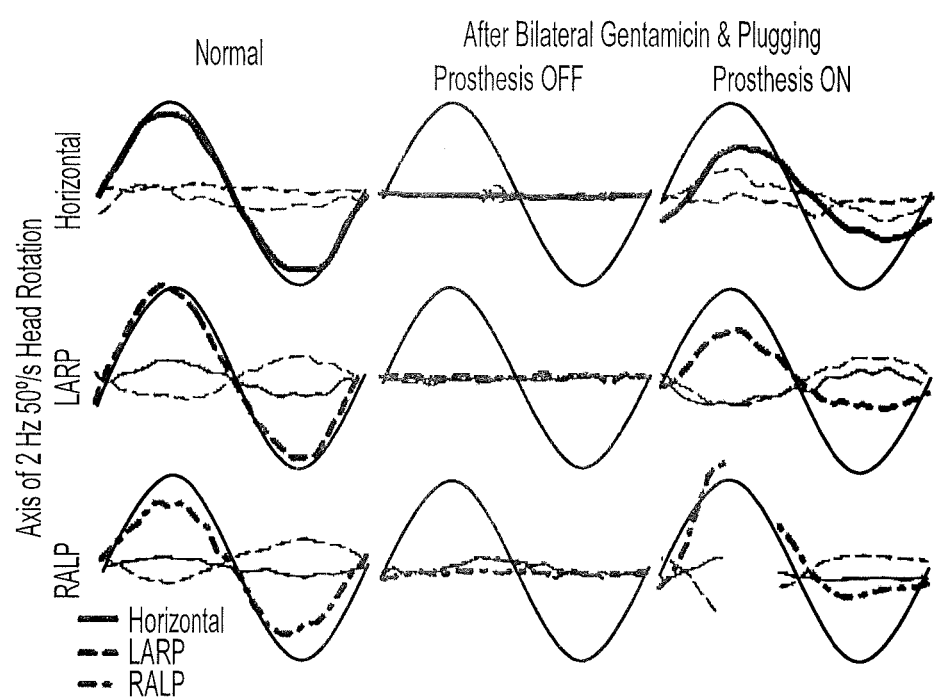
FIG. 12 Mean head and eye angular velocities of a macaque during 2 Hz, 50°/s head rotations in darkness, about the horizontal (top), left-anterior/right-posterior (LARP-middle) and right-anterior/left-posterior (RALP—bottom) SCC axes. Data were recorded after three days of prosthetic stimulation. Red/solid, green/long dash, and blue/short dash traces show the components of eye angular velocity about the horizontal, left superior, and left posterior SCC axes, respectively. Column 1: Prior to lesion. Column 2: After bilateral intratympanic gentamicin treatment to disable normal sensation, plugging all SCCs, and electrode implantation in left labyrinth. Prosthesis pulsing at baseline rate on all channels, but not modulating with head rotation. There are no eye movement responses, consistent with absence of normal sensation. Column 3: With prosthesis modulating to encode gyro signals, after wearing prosthesis 3 days. Standard deviation of each trace at each time point is <10°/s. Traces are inverted about the zero velocity axis as required to facilitate comparison. First half cycle represents excitation of left labyrinth in each case. N=20 cycles for each trace. Blanks indicate removal of nystagmus quick phases, which occur as needed to return the eye toward center position.

The MVP2 is able to restore VOR eye responses in our rhesus macaque. Though the MVP2 can sense 3D translational and rotational motion, we only sense three-dimension rotation and modulate the instantaneous rate of stimulation pulses delivered to the ampullary nerves. We rotated the prosthesis in roughly the horizontal, right-anterior-left-posterior, and left-anterior-right-posterior rotational axes and recorded anticompensatory eye movements in the corresponding axes. FIG. 12 shows time traces of the VOR eye velocities in response to mechanical rotation of the MVP2.

Figure 13:
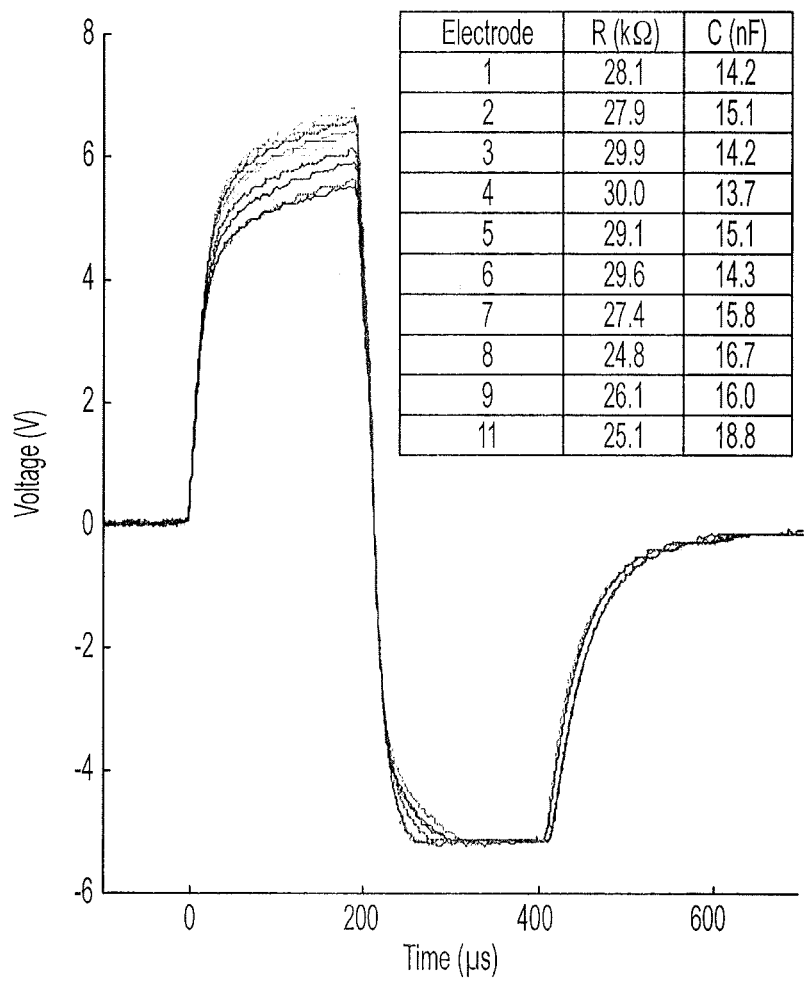
FIG. 13 Potential waveform and corresponding electrode impedances (inset) for each of 10 intralabyrinthine electrodes measured in series with a much larger distant reference (E10) using one embodiment of the invention, which includes the electrode potential amplifier (EPA) within the electronics package of FIG. 2, Within each case, symmetric constant-current biphasic pulses were 150 µA peak and 200 µs per phase.

We measured the potential difference between two stimulating electrodes as a biphasic symmetric pulse with 170 µA current amplitude and 200 µs pulse duration was delivered. FIG. 13 presents the impedance measurements. All electrode impedance measurements have comparable waveforms and magnitudes. We found the electrode's resistance by finding the instantaneous voltage when a pulse was delivered (R=V(t)/I(t)), and we found the electrode's capacitance by calculating the voltage change during the 170 µA square wave (C=I(t)/(dV(t)/dt)). The similar resistances and capacitances across all electrodes are supported by the fact that we designed the electrodes sizes to be of a comparable size.

Figure 14:
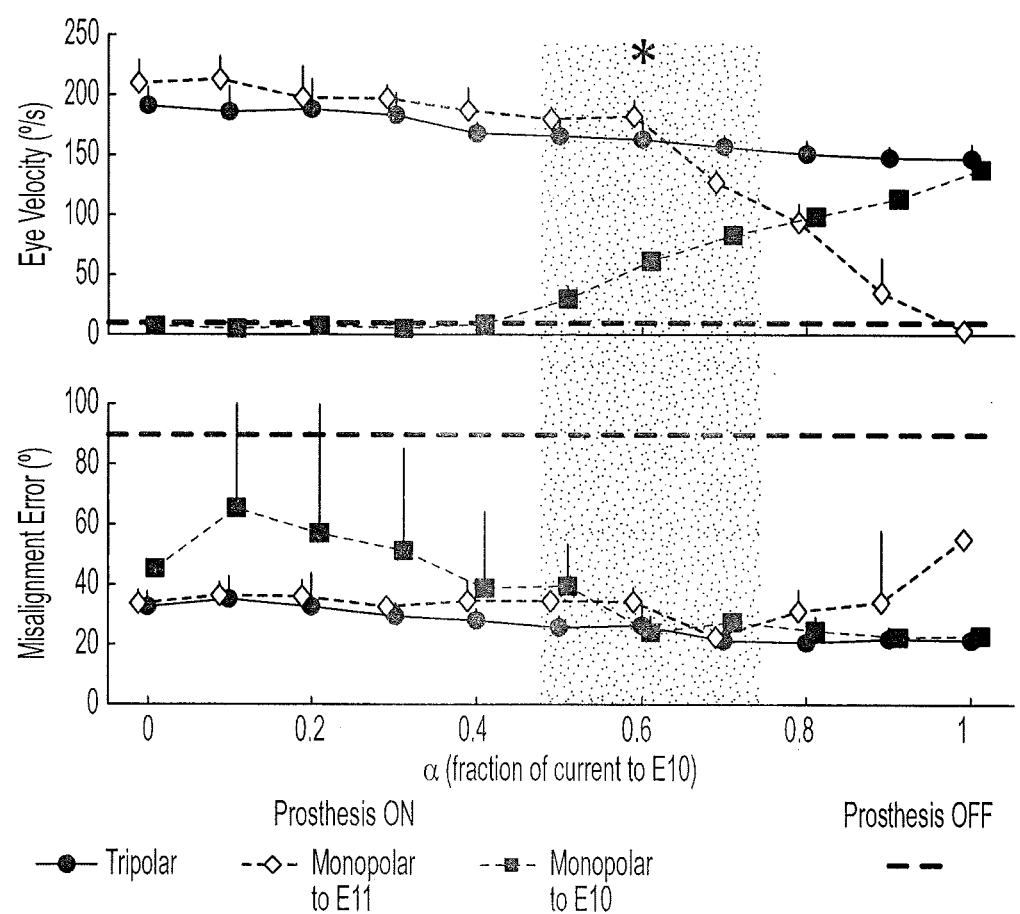
FIG. 14 Eye movements in response to tripolar stimulation using one embodiment of the invention, with varying proportions of a 200 µA/phase, 200 us/phase, biphasic cathodic-first stimulus current pulse (via one electrode on the P electrode array near the left posterior SCC) returned by either a far/muscle reference (square), near/intralabyrinthine reference (diamond), or a proportional distribution between the two (circles), α=fraction of current returned via far reference. During tests, the animal was stationary in darkness, and the vestibular prosthesis was set to modulate pulse rate on the left post as required to simulate a 1 Hz, ±300°/s sinusoidal head rotation about the axis of the left posterior canal. Peak eye movement response amplitude and misalignment (angle between desired and observed 3D axis of eye response) were computed as the mean (±1 standard deviation) for 10 cycles at each α. Asterisk indicates α's at which amplitude was significantly better (p<0.01) than the α=1 case while misalignment was significantly less (p<0.01) than the α=0 case.

The MVP2 has an onboard amplifier that can be used to measure electrode impedances. Biphasic symmetric stimulation pulses with current amplitudes of 170 uA and pulse duration of 200 us were applied to all electrodes with respect to a large electrode implanted in the neck musculature. All electrodes had similar resistances and capacitances (FIG. 13 inset), which confirms the fact that all electrodes have comparable electrode surface areas, FIG. 14 demonstrates the effect of "steering" current from one electrode in the left posterior SCC ampulla by returning different fractions via each of two different return electrodes in a tripolar configuration. Cathodic-first current pulses delivered via electrode E3 versus distant reference E10 alone (i.e., $\alpha=1$, the typical "monopolar" configuration) elicited an aVOR eye responses at 136±7.7°/s peak with misalignment (relative to the RALP axis) of 23+2.7°. Stimuli delivered via E3 to near reference E11 (i.e., $\alpha=0$, a "bipolar" format) elicited a larger aVOR eye response of 209+18°/s, but the misalignment was also greater at 33±4°. For a subset of intermediate a values ($0.5 \geq \alpha \geq 0.7$), it was possible to maintain response amplitude while minimizing misalignment. For comparison, the amplitude and misalignment of aVOR eye responses to RALP rotation in the Prosthesis OFF condition for the same animal. At intermediate percentages of current distribution however, the tripolar stimulation varies greatly from the summation of the bipolar. We theorize this nonlinearity is due in part to the nerve's activation threshold. Because a constant 200 µA is applied regardless of the return electrode locations, we observed no decrease in amplitude as current was phased from one electrode to another. This trend was not true for either bipolar case where the amplitude VOR eye response decreased as current amplitude decreased.

DISCUSSION

Several features of the MVP2 make it a significant advancement towards a clinically applicable, implantable vestibular prosthesis. These include the device's reduced size, lower power consumption, ability to sense rotational and linear motions, ability to current steer, and ability to record eCAPs.

The reduced size of MVP2 allows the device to be placed in a hermetic package of thickness and overall size comparable to cochlear implants currently in clinical use. This is a marked improvement over the MVP1. Considering the recent reductions in cochlear implant stimulator circuitry size, a hybrid cochlear/vestibular implant with both labyrinthine and cochlear electrodes could easily fit into a post-auricular subperiosteal pocket like that used for cochlear implant internal processors. Because the transmastoid approach to SCC ampullae is mostly the same as the approach for cochlear implantation, it can be accomplished by most surgeons already trained to do cochlear implant surgery.

The device's low power consumption allows up to 50 hours of operation on three AAA-sized batteries in a package that is relatively small, light, and flat. Although incorporation of an inductive transcutaneous link for power transmission would incur a ~75-80% reduction in power efficiency compared to the percutaneous connections we have used in animals, the MVP2's nearly 50% reduction in power consumption versus the MVP1 brings it into the range for which a pager-sized 8-battery belt-pack could power the device for >36 hrs through an inductive transcutaneous link or for nearly a week via a percutaneous connector like those used for the Ineraid cochlear implant.

Subperiosteal placement of a vestibular prosthesis sensor/processor a few centimeters posteroinferior of the post-auricular location now commonly used for cochlear implants would approximately align the gyroscopes with the SCCs they are meant to emulate. To measure and pre-compensate for any residual misalignment between the implanted sensors and SCCs, the MVP's tri-axis accelerometer can be used to measure the device's orientation with a resolution up to 0.139° in situ with respect to palpable skull landmarks that can in turn be related to SCC orientations.

Misalignment between SCCs and cardinal response axes due to either non-ideal device orientation or current spread can be corrected via a pre-compensatory linear coordinate system transformation and current steering.

The ability to control several current sources concurrently offers a means to achieve better control over axis misalignment due to channel interaction. Although the complex labyrinthine microanatomy makes it difficult to predict exactly how an electrode's response axis will change when different fractions of that electrode's source current are steered to different returns in a tripolar paradigm, our data confirm that a multipolar, "current steering" paradigm can shift the pattern of ampullary nerve stimulation sufficiently to expand the device's coverage of the 3D space of possible head rotations. If these results are indicative of the ability to manipulate the current between more closely spaced neural populations with more closely spaced electrodes, then current steering could provide a way to improve neural selectivity as in the case of cochlear implants.

The MVP2's onboard amplifier can be used to measure electrode impedances, providing information regarding device integrity and/or electrode migration with the implant in situ and in vivo. Electrode impedances measurements have proven useful in the clinic with cochlear implants users because such measurements provide a means of monitoring electrode integrity and scar formation.

These features new to the field of vestibular prosthetic design have facilitated physiological animal experiments with rhesus macaques. These experiments will help determine necessary features and constraints for eventual use in humans.

Example

Safe Direct Current Stimulation

The present state of the art in vestibular prosthesis technology can only excite activity. This poses a major problem, because a vestibular prosthesis implanted in only one ear can therefore only accurately encode quick head rotations toward that ear by exciting nerve activity. During head rotations in the opposite direction, the prosthesis would ideally inhibit nerve activity, conveying information about the head rotation to the brain. However, this is not possible with the present state of the art. Attempts to simulate inhibition via withdrawal of excitation from above-normal baseline levels have resulted in suboptimal outcomes.

Generally, direct current (DC) stimulation cannot be used in chronically implanted neural prostheses, because it engenders irreversible electrochemical reactions at the metal-saline interface, liberating toxic substances and corroding the electrode. This is a common problem for all chronically implanted stimulating devices, including cochlear implants and pacemakers. This is unfortunate, because DC current stimuli could offer significant potential advantages, especially in the inner ear, which normally maintains a constant (colloquially "DC") electric potential difference between different fluid compartments to drive transduction of auditory and vestibular stimuli by hair cells (the sensory cells of the normal inner ear). Ability to control this DC potential would allow one to both excite and inhibit vestibular nerve responses, whereas the present state of the art in vestibular prosthesis technology can only excite activity. Delivery of low frequency alternating current (LF-AC) would offer similar advantages, but use of LF-AC stimulation is prevented due to the same electrochemistry constraints that prevent use of DC. For small metal electrodes, the current state of the art only allows the long term use of high frequency alternating current (HF-AC) stimuli, typically in the form of brief charge-balanced biphasic current pulses, in chronically implanted neural stimulator systems.

Spelman described an approach to controlling the DC potential of the cochlea using chronically implanted metal electrodes (Spelman, F. Electrodes and Stimulators for Strial Presbycusis. Thirty Fourth Neural Prosthesis Workshop 2010. Oct. 12, 2003; Spelman, F. A., Johnson, T. J., Corbett, S. S., and Clopton, B. M. Apparatus and Method for Treating Strial Hearing Loss. (U.S. Pat. No. 6,694,190 B1). Feb. 17, 2004; Spelman U.S. Pat. No. 6,694,190 B1).

A novel feature of this embodiment of the current invention is repurposing of and novel combination this paradigm in which safe DC stimulation is delivered to the vestibular labyrinth to inhibit vestibular nerve activity so that pulse-rate-modulated biphasic current pulse stimuli, which are exclusively excitatory, can assume greater control of vestibular nerve firing rates. This approach removes spontaneous neural activity from the pattern of activity conveyed to the CNS, giving the novel vestibular prosthesis the unprecedented ability to encode head rotation both toward and away from the implanted labyrinth over a wide range of head velocity.

According to one embodiment of the current invention, we describe a method and apparatus to increase the dynamic range of encoding head motion by suppressing afferent spontaneous activity using a safe version of chronic anodic DC nerve block, and allowing the prosthesis full control over the afferent spike rates. The prosthesis will inhibit native/spontaneous nerve activity and then use LF-AC, HF-AC, or pulse-frequency-modulated (PFM) charge-balanced pulses to achieve complete exogenous control of neuronal baseline action potential firing rates and modulation of the firing rate above and below this baseline in response to head motion.

To improve the VOR eye response when the head moves toward the unimplanted side of the head, we and others in the past attempted increasing the baseline stimulation rate such that it was substantially higher than the afferent spontaneous firing rate and encoding head rotation velocity about this baseline. The hypothetical benefit of this approach is widening of the dynamic range in being able to inhibit the nerve by decreasing the stimulation rate from the artificially high baseline, at the cost of somewhat lower dynamic range in being able to excite the nerve by increasing the stimulation rate. Conceptual idea behind this method is to "recalibrate" the central VOR processes to adapt to an artificially high baseline. The experimental observations show that when the baseline stimulation rate is kept artificially high, the VOR responses are indeed symmetrical; however the amplitudes of the responses are reduced by as much as an order of magnitude. Recent innovative attempts to increase the amplitude of these symmetrical responses were conducted in squirrel monkeys. Over several months, it was possible to modestly increase the gain of the eye response to electrical stimulation from 0.05 to 0.2 by periodically switching chronic stimulation sensitivity between high and low modality (steep vs. shallow mapping between Vs and pulse rate).

Figure 15:
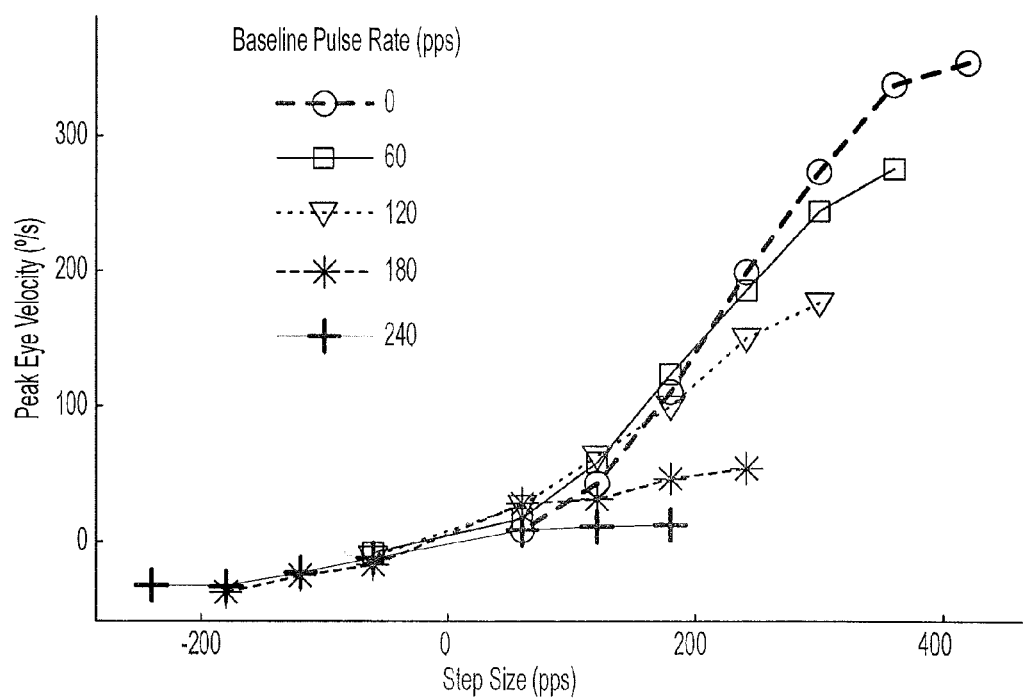
FIG. 15 shows eye velocity in response to step changes in stimulation pulse rate from baseline. Each trace shows the eye responses obtained using a corresponding baseline pulse rate with steps indicated along the X-axis. Increasing pulse rate from a constant baseline pulse rate delivered to the electrode to encode head movement toward the implanted labyrinth evokes a strong eye response. Decreasing the pulse rate from the same baseline to evoke the sensation of head motion away from the implanted labyrinth is significantly less effective.

To better understand why the high baseline rate paradigm is not able to deliver the high amplitude symmetric responses that were hypothesized, we obtained the following data from delivering electrical stimulation to an electrode implanted in the left posterior semicircular canal of a bilaterally vestibular deficient chinchilla. The experimental paradigm consisted of delivering a different baseline stimulation rate to the electrode until the nystagmus ceased, followed by steps of positive or negative rate changes delivered in multiples of 60 pulses per second (pps). FIG. 15 suggests that stimulation paradigms that use higher baseline pulse rates evoke smaller excitatory (positive) eye velocity responses, while the inhibitory (negative) eye responses to the decrease in pulse rate remain relatively similar and small. The plot also indicates improved response symmetry when using higher baseline stimulation rates. Therefore it appears that contrary to the intent of the high baseline stimulation paradigm, the excitatory-inhibitory eye response symmetry seen when using the higher baseline stimulation rates are not due to the increased dynamic range of the inhibitory motion as hoped, but rather due to the decreased dynamic range of the excitatory motion.

Pulses delivered to prosthesis electrodes evoke spikes that increase afferent firing rates above the spontaneous activity already present on the vestibular nerve. For example, when 20-pulse trains at different frequencies are delivered via an electrode implanted near the horizontal branch of the vestibular nerve, the VOR eye responses are unidirectional and have velocities that increase monotonically with pulse rate, suggesting a monotonic increase in firing rate. Additional evidence comes from the visible nystagmus in the direction consistent with increased pulse rate, when the prosthesis is turned on at baseline stimulation rate from power-off state. Finally, experiments with combined nerve stimulation and single recording from the vestibular nucleus in rhesus monkeys showed rate summation of electrically evoked action potentials with the spontaneous firing of the nerve.

It is therefore reasonable to hypothesize that if afferent spontaneous rate could be attenuated, then the prosthesis would be able to more accurately control the baseline spike rate corresponding to stationary head position, as well as to modulate above and below that rate to encode head rotation. Although it may be possible to reduce the spontaneous rate of the vestibular nerve pharmacologically, the most direct methods such as the intra-labyrinthine administration of high concentration doses of aminoglycoside antibiotics have been shown to result in significant damage to neuro-epithelial tissue and cause retrograde degeneration of the vestibular nerve.

Spontaneous activity in the vestibular nerve can be inhibited with anodic DC stimulation. Single unit vestibular nerve recordings from anesthetized squirrel monkeys revealed afferent inhibition in response to short term (5 s) anodic current delivered to a stimulating electrode positioned in the perilymphatic space near the vestibular nerve and a return electrode positioned in the middle ear.

Figure 16:
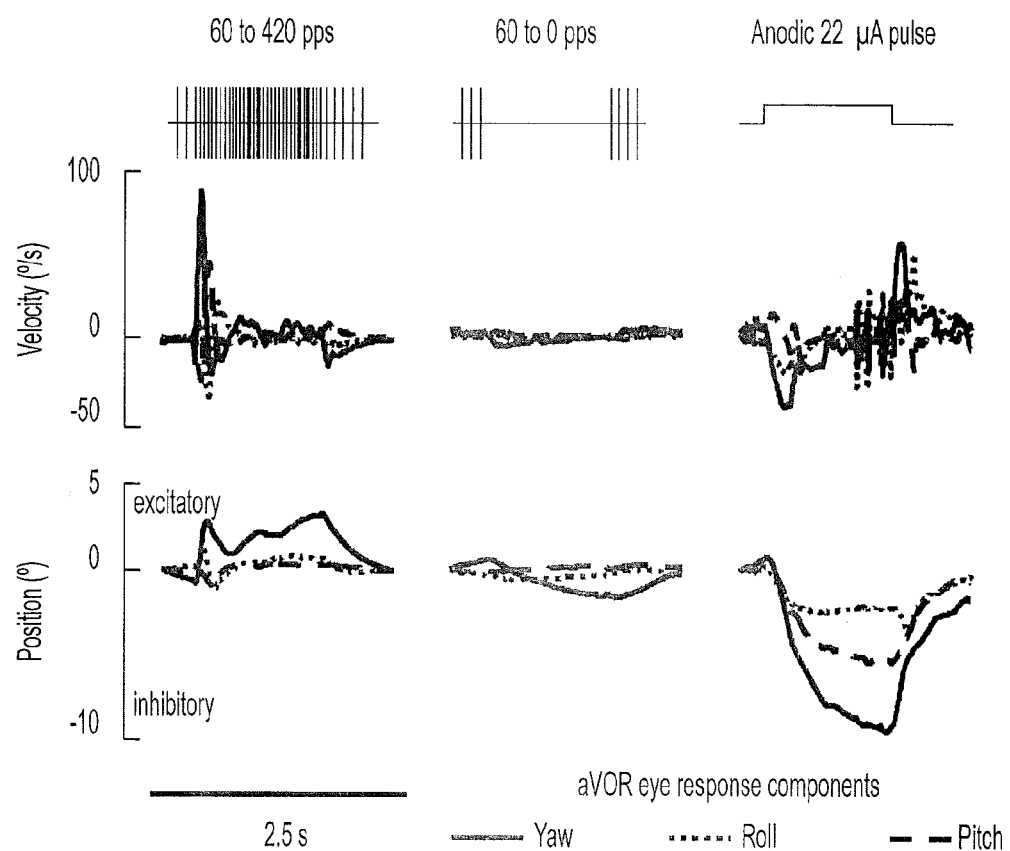
FIG. 16 shows a comparison of VOR responses to three types of stimuli delivered to the same monopolar stimulating electrode implanted in the right horizontal SCC, with the large surface area return electrode positioned in the muscle. Compared to decreasing pulse rate from a baseline of 60 pulses/sec (second column), anodic direct current (DC) stimulus (third column) evokes much stronger inhibition of the vestibular nerve indicative of head movement away from the implanted labyrinth.

To gain confidence that anodic DC stimulation current will be able to inhibit afferent spontaneous activity in a vestibular deficient chinchilla we conducted a preliminary experiment. We compared the eye movements in response to a 2.5 s anodic stimulation pulse delivered to the electrode implanted in the right horizontal semicircular canal to the eye movements elicited when the stimulation rate was increased from the 60 pps baseline to 420 pps, and correspondingly decreased in pulse rate from 60 pps baseline to 0 pps. The responses in FIG. 16 are averaged from 10 trials. The positive values indicate VOR eye movement responses to evoked sensation of head motion toward the stimulated labyrinth and the negative values indicate VOR eye responses to head rotation away from it. The plot shows that the anodic stimulation was able to evoke a strong inhibitory VOR eye response. The ability to evoke a strong inhibitory response using anodic stimulation is consistent with the hypothesis that the spontaneous activity is indeed present on the vestibular nerve and that this activity can be inhibited with anodic DC stimulation more effectively than with a step decrease in pulse rate from 60 pps baseline to 0 pps.

Delivering chronic DC stimulation in the body is toxic because of gas generation by electrolysis, Faradaic charge transfer and electroplating. A particular problem of chronic DC stimulation is the accumulation of ions at the electrode sites, causing ion concentration differences to which neural tissue is particularly sensitive.

Figure 17:
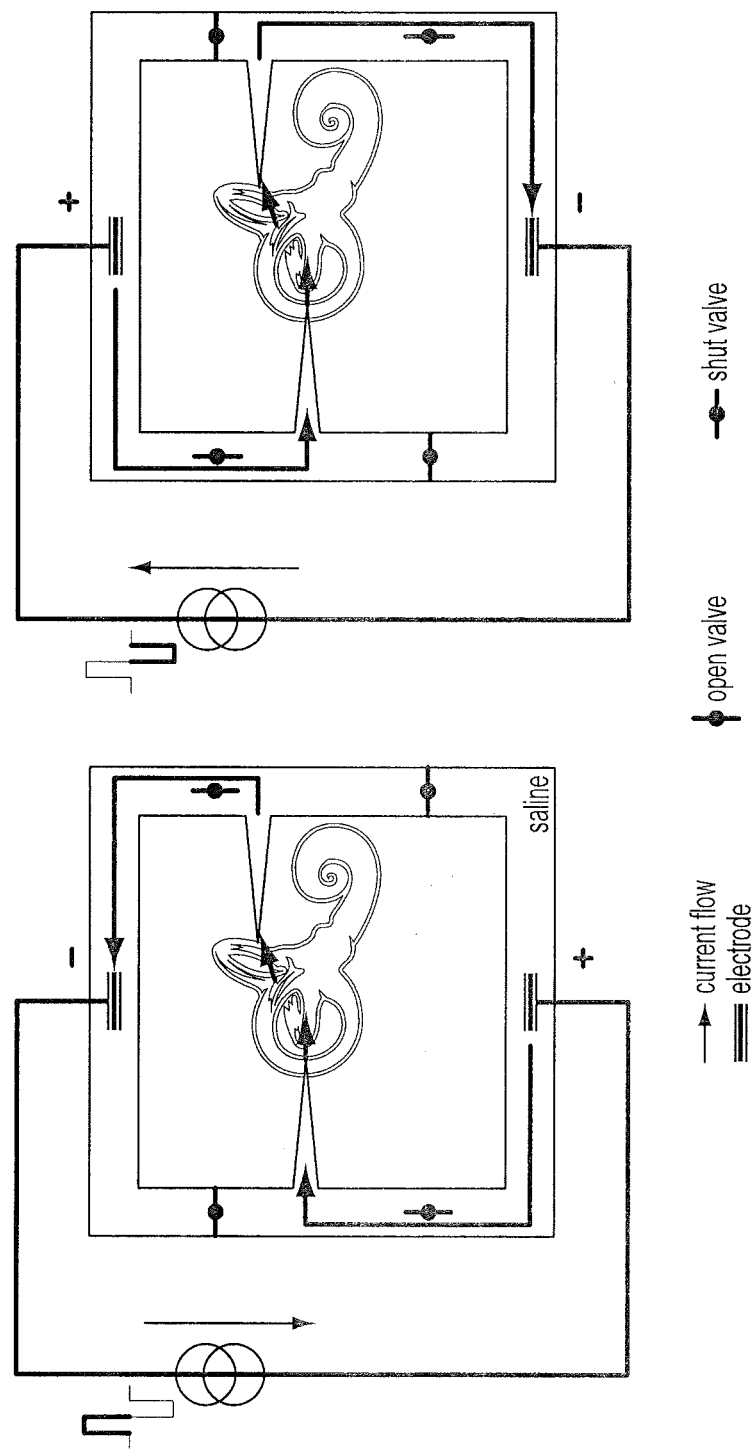
FIG. 17 illustrates the SDCS concept according to an embodiment of the current invention. The two panels represent two states of the same device. In the panel on the left the current flows from the lower electrode to the upper electrode. In the state on the right the current reverses direction. However, because the valves change state along with the electrical current direction, the ionic DC current flows through the electrode tubes from left to right through the labyrinth in both panels.

A solution to the problem of safety in chronic DC stimulation has been described by Spelman et al. initially intended to support endocochlear potential as a potential therapy for strial hearing loss. The authors proposed using a bridge-rectifier-like system in order to overcome the toxic effects of DC current stimulation. The system delivers alternating current (AC) to two electrodes housed in a saline filled chamber and simultaneously modulates four valves to create DC flow of ions at the output of the device. The DC current therefore never flows through the electrodes and the problems associated with electrochemical interactions are avoided. We propose to test the hypothesis that using safe DC stimulation to block afferent spontaneous activity along the vestibular prosthesis stimulation will encode a wider range of head velocities than stimulating with prosthesis alone, Conceptually, the safe DC stimulator (SDCS) delivers alternating current pulses to the electrodes suspended at the opposite ends of a torus filled with artificial perilymph (termed "saline" in FIG. 17). With each change in stimulation polarity, the valves on either side of each electrode change from open-to-closed and closed-to-open, effectively modulating between low impedance and a high impedance path for ionic flow through each valve. Two extension tubes connect to the sides of the torus, such that they can be directed into any tissue to complete the ionic current circuit. FIG. 17 demonstrates this concept comparing the two states of the apparatus. In both, the left and the right panels of the figure, the current flows from left to right through the stimulated tissue. In this way, a continuous AC square wave controlling the apparatus will deliver DC ionic current through the tissue from left to right. This system also addresses the problem of ionic buildup by creating a closed-circuit path for the ions to flow, so that the anions that flow into the electrode tube on the right are replaced by the anions that flow out of the electrode tube on the left.

The tubes that deliver the DC current to the labyrinth in FIG. 17 can be attached to the implanted device that implements the SDCS valve mechanism described in the figure. This device can be implemented together with the vestibular prosthesis to deliver chronic DC stimulation to the vestibular labyrinth in order to deliver chronic DC stimulation to suppress spontaneous firing of the nerve according to an embodiment of the current invention. In one embodiment of the SDCS connection to the labyrinth, the two tubes carrying the DC current will be inserted along with the electrode described in FIG. 3. In another, the two tubes can be assembled into the electrode described in FIG. 3 along a lumen of the electrode leads.

An embodiment of the device would include:
1) fluid channels and electrodes made of biocompatible materials (such as plastic, siloxane, PDMS, silicone, polyimide, silicon nitride, silicon, gold, Pt, Ir, Teflon®/PTFE, glass, or other insulating materials), micro- or mini-machined using photolithographic, 3D printing, laser ablation, traditional machining, eutectic metal removal (or analogous "lost wax" type process), or related approaches to create the functional equivalent of the device described in FIG. 17 in a package small enough to permit implantation in the ear or similar sized body spaces;
2) either a single common fluidic channel for delivery of ionic current to the body space (with respect to a counter sink elsewhere) or a multipolar fluidic channel (including two or more single fluidic channels, allowing both injection and extraction of cationic and/or anionic species from the body compartment of interest);
3) a "chamber electrode" comprising a large-area metal/saline interface connected via a fluid channel within an insulator to a smaller cross-sectional area port in the insulator, so that high current density can be achieved at the port without violating safe-stimulation charge-balance criteria at the metal/saline interface;
4) a "chamber electrode" as in #3, with a hydrogel or other medium filling the chamber to prevent ingress of bacteria
5) an optional optical stimulator that, in concert with chronic inhibition by a "safe-DC" source, drives neural activity at arbitrarily high or low rates; and
6) a controller capable of delivering multi-frequency stimuli, including "safe DC", "safe LF-AC", HF-AC, and pulse frequency modulated charge-balanced pulses, alone or in combination, to override and then completely control the firing rates of tissues of interest.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied without departing from the invention, as would be appreciated by those skilled in the art in light of the above teachings. It is therefore to be understood that, within the scope of the claims and their equivalents, the invention may be practiced otherwise than as specifically described.

We claim:
1. An ionic tissue stimulator comprising:
   an ionic current circuit comprising first and second electrode tubes configured to be ionically coupled to tissue; and
   an AC power supply electrically coupled to and adapted to apply AC electrical voltage or current to said ionic current circuit,
   wherein said ionic current circuit has a first configuration while said AC power supply is in a first polarity that provides a closed-circuit path for a flow of ions between said first and second electrode tubes such that anions that flow into said first electrode tube are replaced by anions that flow out of said second electrode tube, and
   wherein said ionic current circuit has a second configuration while said AC power supply is in a second polarity that provides a closed-circuit path for said flow of ions between said first and second electrode tubes such that anions that flow into said first electrode tube are replaced by anions that flow out of said second electrode tube such that a DC ionic current is provided to said tissue in response to said AC electrical voltage.

2. The ionic tissue stimulator of claim 1, wherein said ionic current circuit is filled with an ionic current conducting medium.

3. The ionic tissue stimulator of claim 2, wherein the ionic current conducting medium is either an artificial perilymph solution or a saline solution.

4. The ionic tissue stimulator of claim 1, further comprising first and second electrodes suspended in said ionic current circuit.

5. The ionic tissue stimulator of claim 4, further comprising a plurality of valves operatively arranged within said ionic current circuit.

6. The ionic tissue stimulator of claim 5, wherein the plurality of valves are arranged on either side of the first and second electrodes.

7. The ionic tissue stimulator of claim 5, wherein the plurality of valves change from open-to-closed and closed-to-open with each change in polarity.

8. The ionic tissue stimulator of claim 5, wherein the plurality of valves are modulating between a low impedance path and a high impedance path for the flow of ions through each valve.

9. The ionic tissue stimulator of claim 1, wherein the ionic current circuit is configured to be surgically implanted in said tissue to form said closed-circuit path with at least a portion of said tissue intercepting said flow of ions.

10. The ionic tissue simulator of claim 1, further comprising a controller operatively connected to said AC power supply.

11. The ionic tissue stimulator of claim 1, wherein the tissue is a vestibular labyrinth.

12. The ionic tissue stimulator of claim 1, wherein DC stimulation is applied chronically to suppress spontaneous firing of a nerve.

13. The ionic tissue stimulator of claim 1, further comprising a vestibular prosthesis operatively connected to said ionic tissue stimulator.

* * * * *